United States Patent
Hansen et al.

(10) Patent No.: US 11,819,482 B2
(45) Date of Patent: Nov. 21, 2023

(54) COMPOSITION COMPRISING SUPLATAST TOSILATE

(71) Applicants: Conrig Pharma ApS, Copenhagen (DK); Solural Pharma ApS, Ballerup (DK)

(72) Inventors: John Bondo Hansen, Copenhagen (DK); Mikael Søndergård Thomsen, Hvidovre (DK); Bent Højgaard, Allerød (DK)

(73) Assignees: Conrig Pharma ApS, Copenhagen N (DK); Solural Pharma ApS, Ballerup (DK)

( * ) Notice: Subject to any disclaimer, the term of this patent is extended or adjusted under 35 U.S.C. 154(b) by 308 days.

(21) Appl. No.: 16/641,524

(22) PCT Filed: Aug. 28, 2018

(86) PCT No.: PCT/EP2018/073123
§ 371 (c)(1),
(2) Date: Feb. 24, 2020

(87) PCT Pub. No.: WO2019/042995
PCT Pub. Date: Mar. 7, 2019

(65) Prior Publication Data
US 2020/0230083 A1    Jul. 23, 2020

(30) Foreign Application Priority Data

Aug. 29, 2017    (EP) .................................. 17188229

(51) Int. Cl.
*A61K 31/167*    (2006.01)
*A61K 45/06*    (2006.01)
(Continued)

(52) U.S. Cl.
CPC .......... *A61K 31/167* (2013.01); *A61K 9/5084* (2013.01); *A61K 9/0053* (2013.01);
(Continued)

(58) Field of Classification Search
CPC .. A61K 31/167; A61K 9/5084; A61K 9/0053; A61K 9/209; A61K 9/2866; A61K 45/06; A61K 9/2072; A61K 9/2086
See application file for complete search history.

(56) References Cited

U.S. PATENT DOCUMENTS

| 4,556,737 A | 12/1985 | Koda et al. |
| 4,670,583 A | 6/1987 | Koda et al. |

(Continued)

FOREIGN PATENT DOCUMENTS

| CN | 102210688 A | 10/2011 |
| JP | B1991070698 | 9/1984 |

(Continued)

OTHER PUBLICATIONS

Brown et al., Chest 129: S180-185 (2006).
(Continued)

*Primary Examiner* — Savitha M Rao
*Assistant Examiner* — Andrew P Lee
(74) *Attorney, Agent, or Firm* — Dinsmore & Shohl LLP; Weston R. Gould

(57) ABSTRACT

Provided is a pharmaceutical composition comprising suplatast tosilate or pharmaceutically acceptable derivatives thereof that provides for a constant exposure of the compound.

20 Claims, 11 Drawing Sheets

Figure 1A:
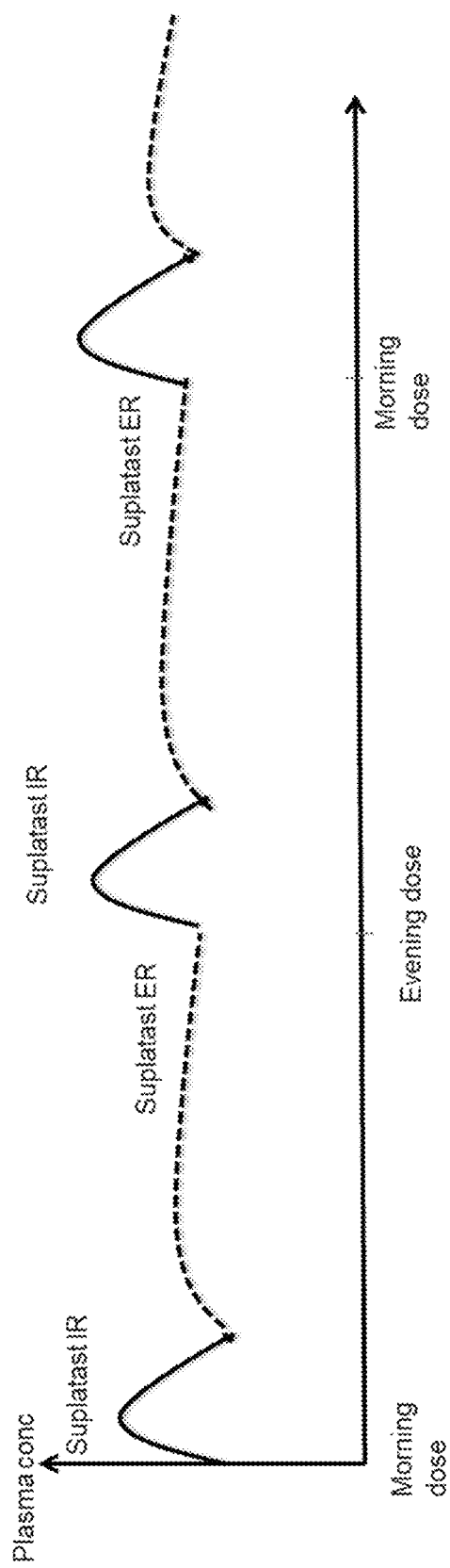

(51) Int. Cl.
 A61K 9/50 (2006.01)
 A61K 9/00 (2006.01)
 A61K 9/24 (2006.01)
 A61K 9/28 (2006.01)
(52) U.S. Cl.
 CPC ............ *A61K 9/209* (2013.01); *A61K 9/2866* (2013.01); *A61K 45/06* (2013.01)

(56) References Cited

U.S. PATENT DOCUMENTS

| | | | |
|---|---|---|---|
| 7,897,645 | B2 | 3/2011 | Ogawa et al. |
| 2003/0180352 | A1* | 9/2003 | Patel ................. A61K 9/1617 424/465 |
| 2016/0354315 | A1* | 12/2016 | Li ....................... A61K 9/2031 |
| 2019/0254998 | A1* | 8/2019 | Hansen ................ A61K 31/167 |

FOREIGN PATENT DOCUMENTS

| | | | |
|---|---|---|---|
| JP | 1997500645 | A | 1/1997 |
| JP | 2000507613 | A | 6/2000 |
| JP | 2002179554 | A | 6/2002 |
| JP | 2002523358 | A | 7/2002 |
| JP | 2002370968 | A | 12/2002 |
| JP | 2002541186 | A | 12/2002 |
| JP | 2006131521 | A | 5/2006 |
| JP | 2006335771 | A | 12/2006 |
| JP | 2011246454 | A | 12/2011 |
| WO | 1999/33448 | A1 | 7/1999 |
| WO | 2002/087549 | A1 | 11/2002 |
| WO | 2003/057198 | A1 | 7/2003 |
| WO | 2005/105055 | A1 | 11/2005 |
| WO | 2008/061226 | A2 | 5/2008 |
| WO | 2011/005352 | A1 | 1/2011 |
| WO | 2017/032384 | A1 | 3/2017 |
| WO | 2017108041 | A1 | 6/2017 |

OTHER PUBLICATIONS

Van Manen et al., Eur. Respir. Rev. 25: 278-286 (2016).
Yang et al., Chin. J. Tuberc. Respir. Dis. 38(12): 928-933 (2015).
Fukahara et al., "Suplatast Tosilate Protects the Lung Against Hyperoxic Lung Injury by Scavenging Hydroxyl Radicals", Free Radic Biology and Medicine, vol. 106, 1-9, 2017.
Izumi et al., "Suplatast Tosilate Reduces Radiation-Induced Lung Injury in Mice Through Suppression of Oxidative Stress," Free Radical Biology and Medicine, vol. 136, 52-59, 2019.
Yoshihisa Ishiura et al., Effect of an Orally Active Th2 Cytokine Inhibitor, Suplatast Tosilate, on "Atopic Cough"; Drug Research 2008; 58(6): 297-302.
Luca Richeldi et al., Efficacy and Safety of Nintedanib in Idiopathic Pulmonary Fibrosis; The New England Journal of Medicine, May 29, 2014, vol. 370, No. 22, 2071-2082.
Arata Azuma et al., Exploratory analysis of a phase III trial of pirfenidone identifies a subpopulation of patients with diopathic pulmonary fibrosis as benefiting from treatment; Respiratory Research 2011, 12:143, 1-11.
Makoto Furonaka et al., Suplatast Tosilate Prevents Bleomycin-Induced Pulmonary Fibrosis in Mice; J Pharmacol Exp Ther. Jan. 2009, 328(1): 55-61.
Jian-Rong Zhou et al., Novel Antitussive Effect of Suplatast Tosilate in Guinea Pigs, Pharmacology, 2015; 95(1-2): 36-41.
Yoshihisa Ishiura, Th2 cytokine inhibition and cough in asthmatic and bronchitic patients; Ann Med 2004; 36:623-629.
Joan Antoni Fernandez-Blanco et al., Enhanced cough reflex in a model of bleomycin-induced lung fibrosis in guinea pigs; Clinical Science (2015) 129, 1001-1010.
Won-Serk Kim et al., Accelerated Wound Healing by S-Methylmethionine Sulfonium: Evidence of Dermal Fibroblast Activation via the ERK1/2 Pathway; Pharmacology 2010, 85:68-76.
Karen Methling et al., Investigation of the In Vitro Metabolism of the Analgesic Flupirtine; Drug Metabolism and Disposition, 2009, 37:479-493.
Hideaki Miyamoto et al., Usefulness of suplatast tosilate for chronic cough following lung cancer surgery; Gen Thorac Cardiovasc Surg (2009) 57:463-466.
A.H. Morice et al., ERS guidelines on the assessment of cough; Eur Respir J 2007; 29: 1256-1276.
S. Myou et al., Effects of suplatast tosilate, a new type of anti-allergic agent, on airway cough hypersensitivity induced by airway allergy in guinea-pigs; Clinical and Experimental Allergy, 2001, vol. 31, 1939-1944.
Takanobu Shioya et al., Effect of suplatast tosilate, a Th2 cytokine inhibitor, on cough variant asthma; Eur J Clin Pharmacol (2002) 58:171-176.
Akio Suzuki et al., Identification of Human Cytochrome P-450 Isoforms Involved in Metabolism of R(+)- and S(−)-Gallopamil: Utility of In Vitro Disappearance Rate; Drug Metabolism and Disposition, 1999, vol. 27, No. 11, 1254-1259.
Yukio Tada et al., Synthesis and Antiallergic Activity of Dimethyl-2-(phenylcarbamoyl)ethylsulfonium p-Toluenesulfonate Derivates; J. Med. Chem. 1998, 41, 3330-3336.
Tohda, Y. et al., Effects of suplatast tosilate (IPD Capsules®) on the production of active oxygen by neutrophils and of IL-8 by mononuclear cells, International Immunopharmacology, 1: 1183-1187, 2001.
Saito, Y., The Long-term Effect of Suplatast Tosilate in the Patients with Pulmonary Fibrosis, Chest 138(4_Meeting Abstracts), Oct. 2010.

* cited by examiner

COMPOSITION COMPRISING SUPLATAST TOSILATE

CROSS REFERENCE TO RELATED APPLICATIONS

This application is a U.S. National Stage of international application PCT/EP2018/073123 filed Aug. 28, 2018, which claims priority to European Application No: 17188229.3 filed Aug. 29, 2017, the entire contents of each of which are incorporated herein by reference.

TECHNICAL FIELD

The present invention relates to a pharmaceutical composition comprising suplatast tosilate, or a pharmaceutically acceptable derivative thereof, formulated to achieve acute and sub-chronic effects of said suplatast tosilate.

BACKGROUND

Suplatast tosilate ((±)-3-{[4-(3-ethoxy-2-hydroxy-propoxy)phenyl]amino}-3-oxopropyl)(dimethyl)sulfonium; 4-methylbenzenesulfonate) (abbreviated ST herein) is a drug marketed in Japan for oral treatment of atopic dermatitis, asthma and allergy (rhinitis). It is characterized by its ability to inhibit Th2 cytokine production and by its high degree of safety. It has been shown in several pre-clinical and clinical studies that ST could have beneficial effects in several other disorders, especially disorders that are associated with Th2 inflammation and hyper-eosinophilia.

The normal dosing of ST is three times daily, and most studies indicate that the compound should be administered for at least 2 weeks in order to obtain efficacy. Other studies point to acute and sub-chronic effects in addition; for example, a single dose of ST reduces cough in animal models.

Other studies have shown a pronounced and dose dependent effect of ST on mechanisms important for development of inflammation and fibrosis. This indicates that provided that the exposure of ST is sufficient at relevant organs, the compound could have an acute effect on diseases characterized by inflammation, fibrosis and hyper-eosinophilia in general.

In asthma patients, symptoms include episodes of wheezing, coughing, chest tightness, and shortness of breath. These episodes may occur a few times a day or a few times per week. Depending on the person they may become worse at night or with exercise.

Atopic dermatitis, also known as atopic eczema, is a type of inflammation of the skin (dermatitis). It results in itchy, red, swollen, and cracked skin. The condition typically starts in childhood with changing severity over the years. Scratching worsens symptoms and affected people have an increased risk of skin infections. Furthermore, many people with atopic dermatitis develop hay fever or asthma. Many patients suffer from itching and scratching during night.

In allergic rhinitis patients, symptom onset is often within minutes following exposure and they can affect sleep, the ability to work, and the ability to concentrate at school and life in general.

In common for these patients is that a full day and/or full night coverage will improve quality of life.

SUMMARY

In common for the above-mentioned conditions is that an acute and a sub-chronic effect of suplatast tosilate (ST) will secure optimal efficacy in achieving a benefit in the quality of life of the patients.

The present inventors now find that continuous efficacy coverage of suplatast tosilate can be achieved within one dose setting, with reducing dosing frequency and improving patient compliance, while at the same time supporting the immediate effects on disease symptoms. The present invention provides a pharmaceutical formulation that provides a bolus dose and release of suplatast tosilate as well as an extended release profile of suplatast tosilate to achieve this objective.

The present pharmaceutical formulation may be administered once daily or twice daily at times that will secure optimal effect in benefit of the quality of life of the patients. This could be in the morning to facilitate a good start of the working day, and in the evening to secure a good night's sleep. Both acute and sub-chronic effects of the drug can thus be obtained with only twice daily administration. In addition, to alleviate acute symptoms the present pharmaceutical formulation may be administered as needed; in addition to the once or twice daily administration.

It is an aspect of the present disclosure to provide a pharmaceutical composition comprising a compound of formula (I):

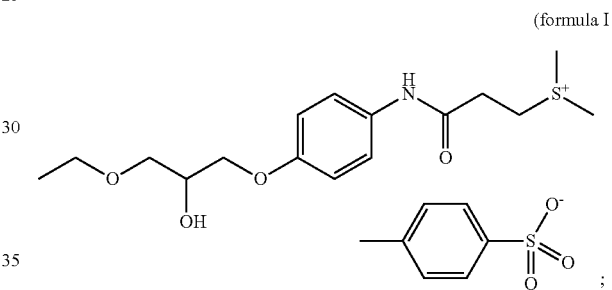

(formula I)

suplatast tosilate), or a pharmaceutically acceptable derivative thereof,
said composition comprising, separately or together;
a. a first release component comprising said compound and providing for extended release of said compound, and
b. a second release component comprising said compound and providing for immediate release of said compound.

In one embodiment said composition is to be administered in the morning and/or in the evening/prior to sleep to alleviate sub-chronic or chronic symptoms of disease; and optionally as required to alleviate emerging acute symptoms of disease.

DRAWINGS

FIG. 1A: Pharmacokinetic profile of a composition comprising an immediate-release and an extended-release component each comprising suplatast tosilate; dosed in the morning and in the evening to maintain a steady exposure.

Figure 1B:
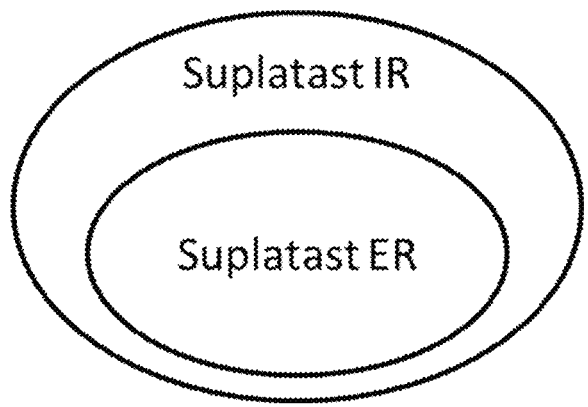

FIG. 1B: An embodiment of the present disclosure of a pharmaceutical composition comprising an extended release (ER) core and an immediate release (IR) coating.

Figure 1C:
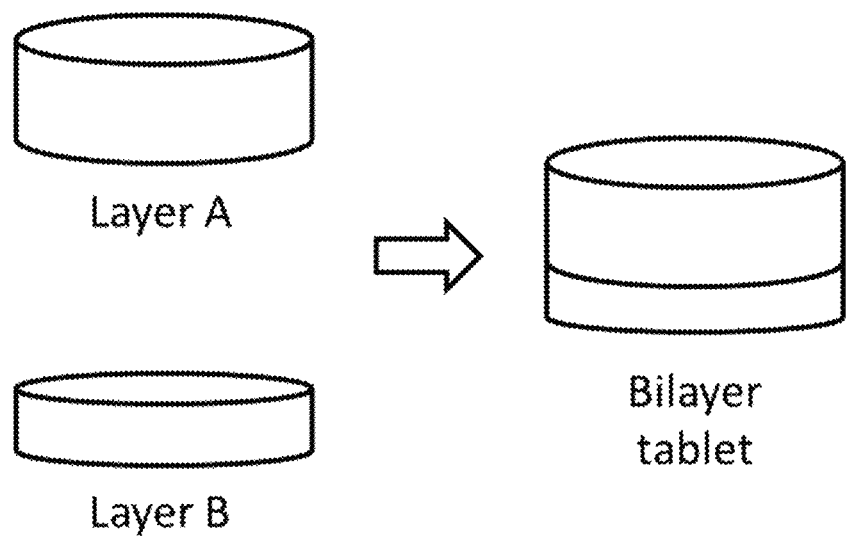

FIG. 1C: An embodiment of the present disclosure of a pharmaceutical composition comprising an individual extended release (ER) Layer A and an individual immediate release (IR) Layer B which are compressed on top of one another to form a bilayer tablet.

Figure 2:
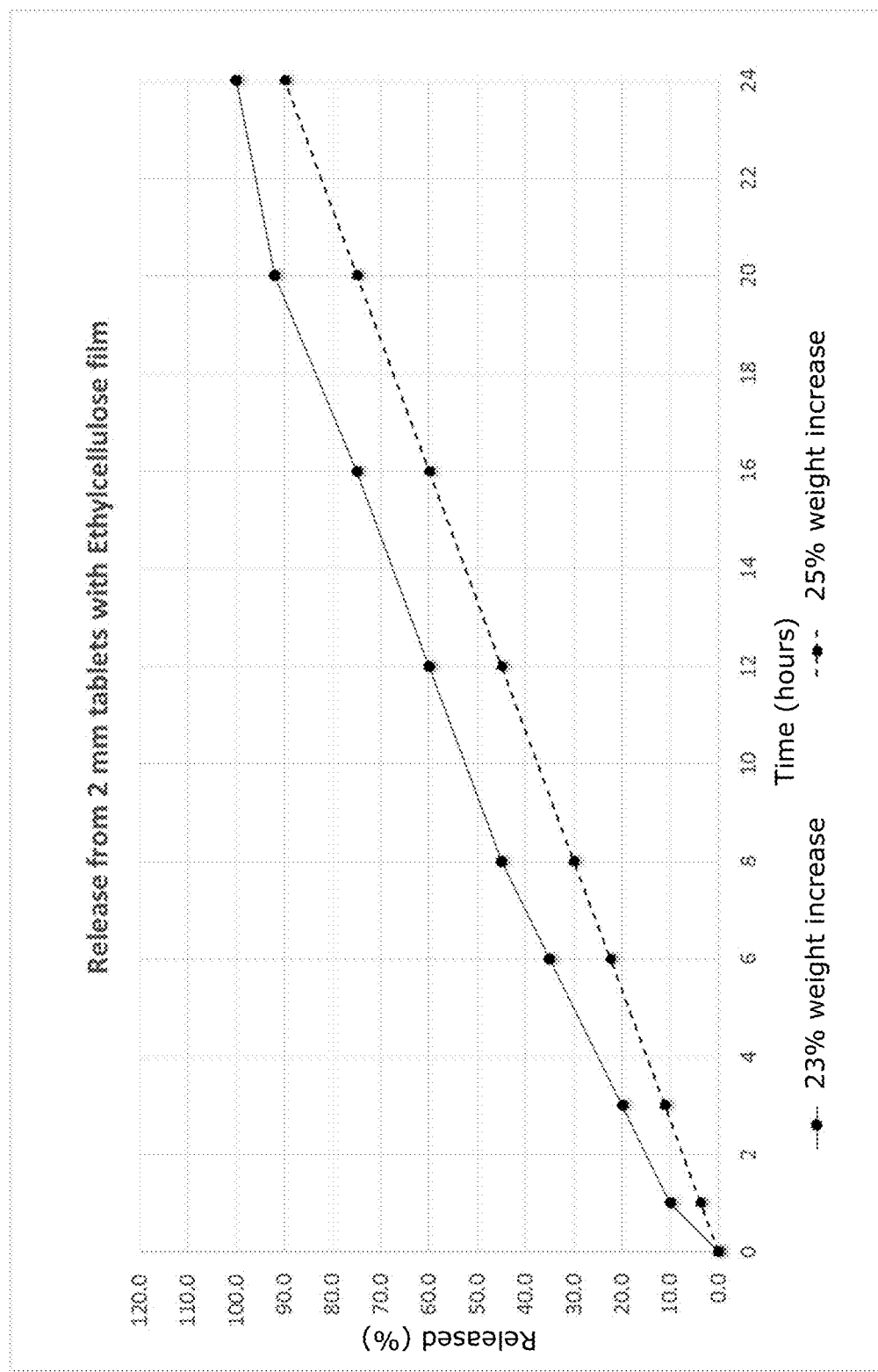

FIG. 2: Expected release profile of suplatast tosilate mini-tablets coated with ethyl cellulose film (cf. Example 1).

Figure 3:
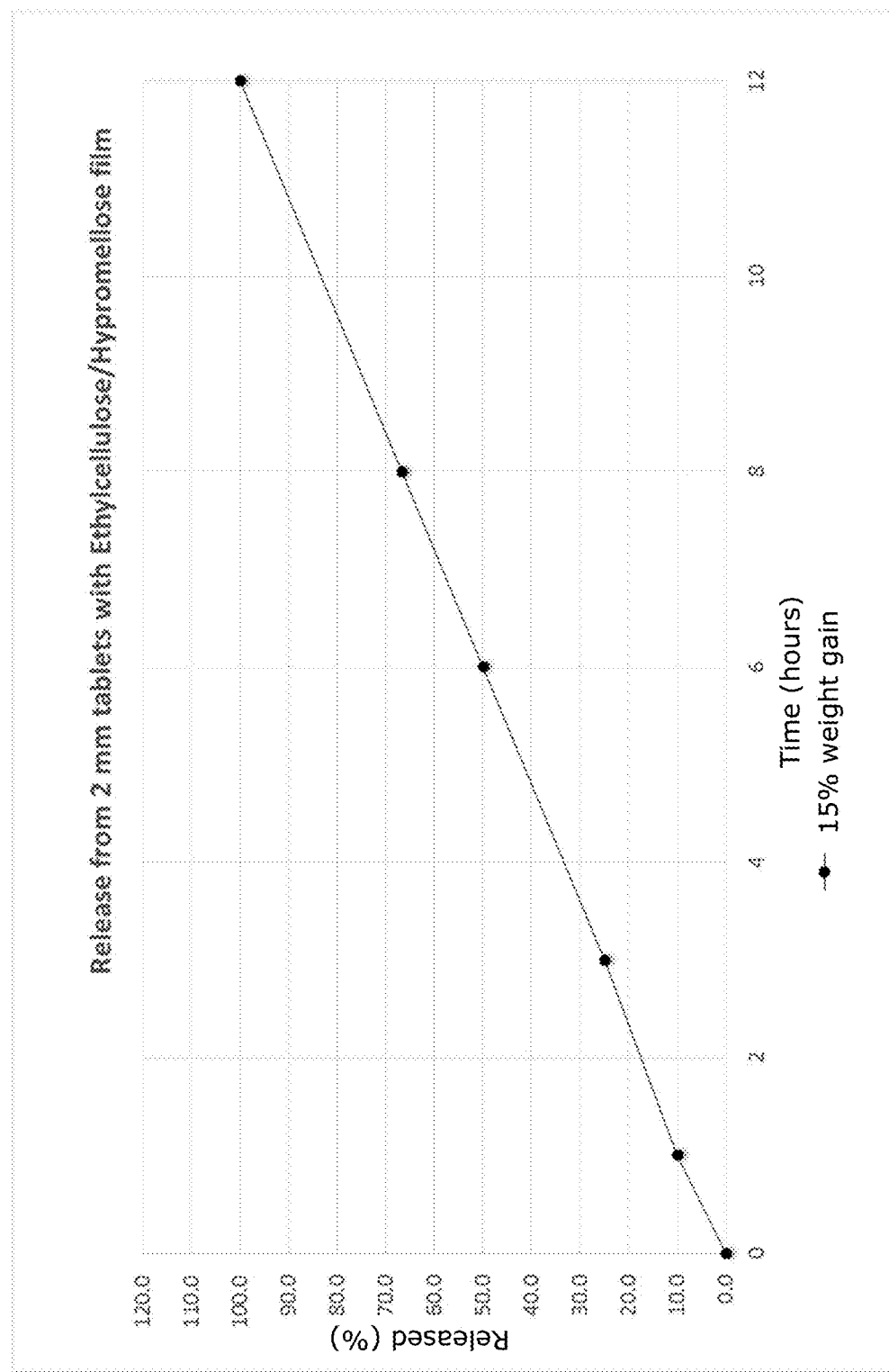

FIG. 3: Expected release profile of suplatast tosilate mini-tablets coated with ethyl cellulose/hypromellose film (cf. Example 2).

Figure 4:
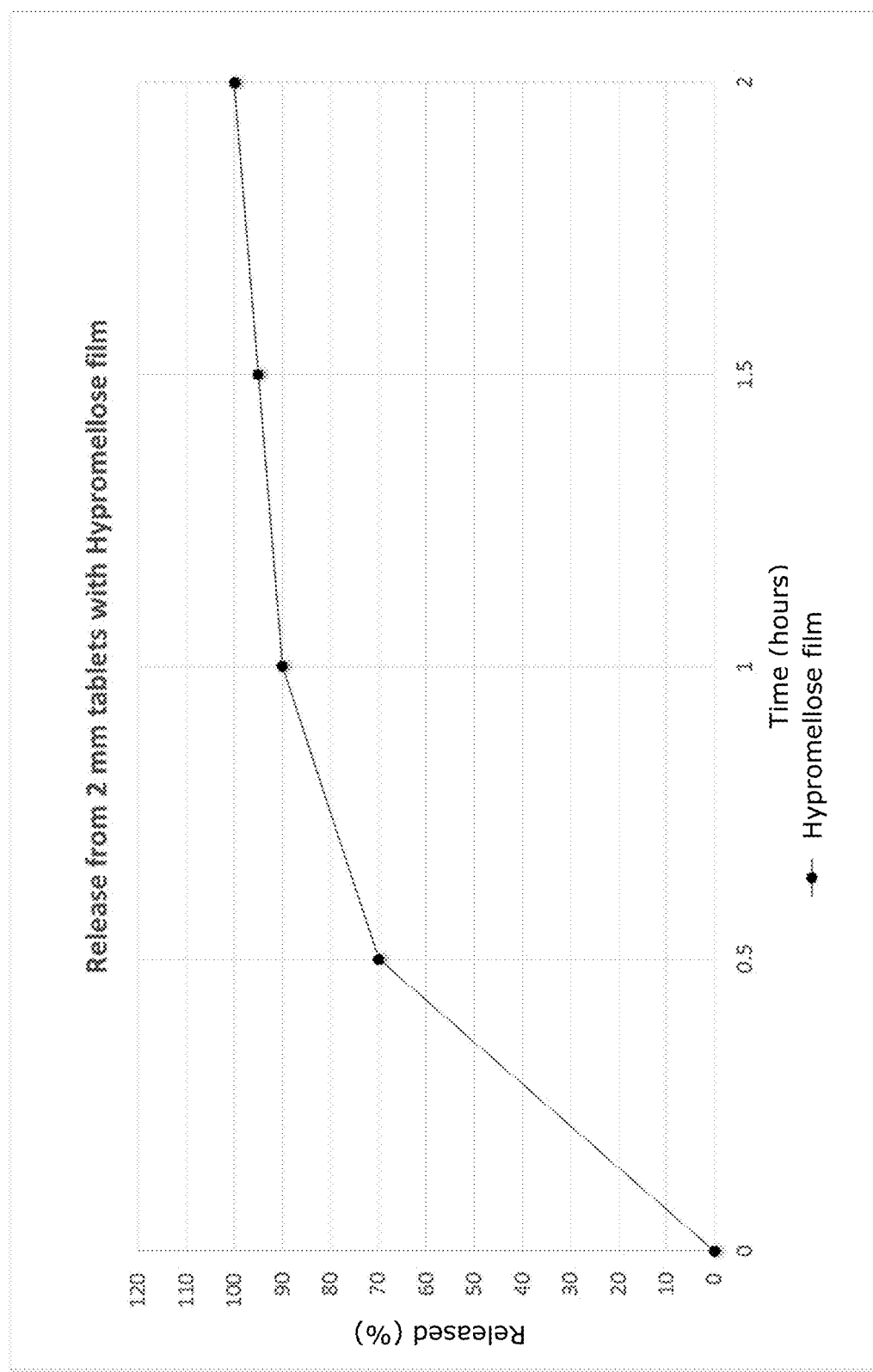

FIG. 4: Expected release profile of suplatast tosilate mini-tablets coated with hypromellose film (cf. Example 3).

Figure 5:
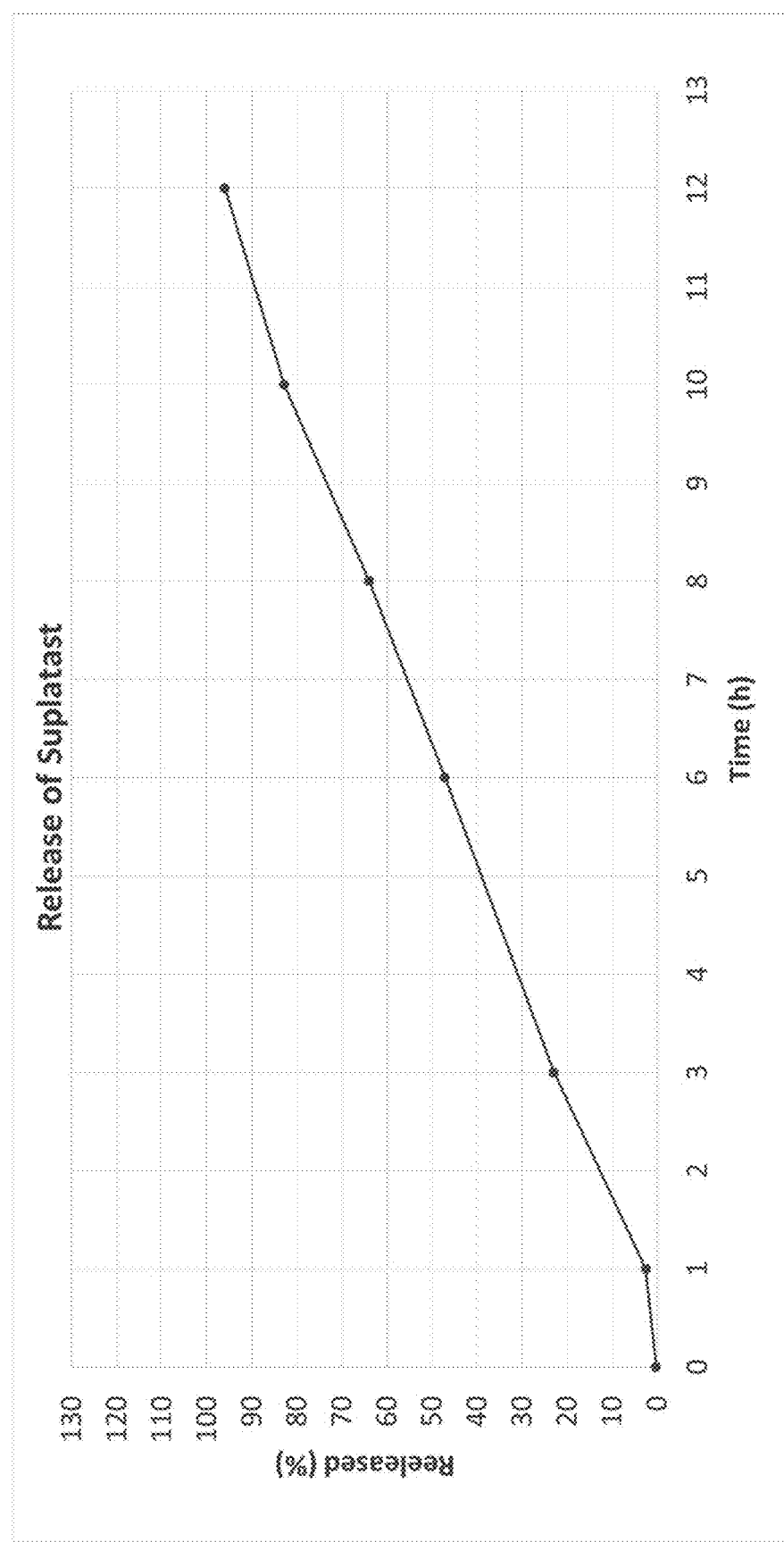

FIG. 5: Release profile of suplatast tosilate mini-tablets coated with ethyl cellulose film—ER (cf. example 10).

Figure 6:
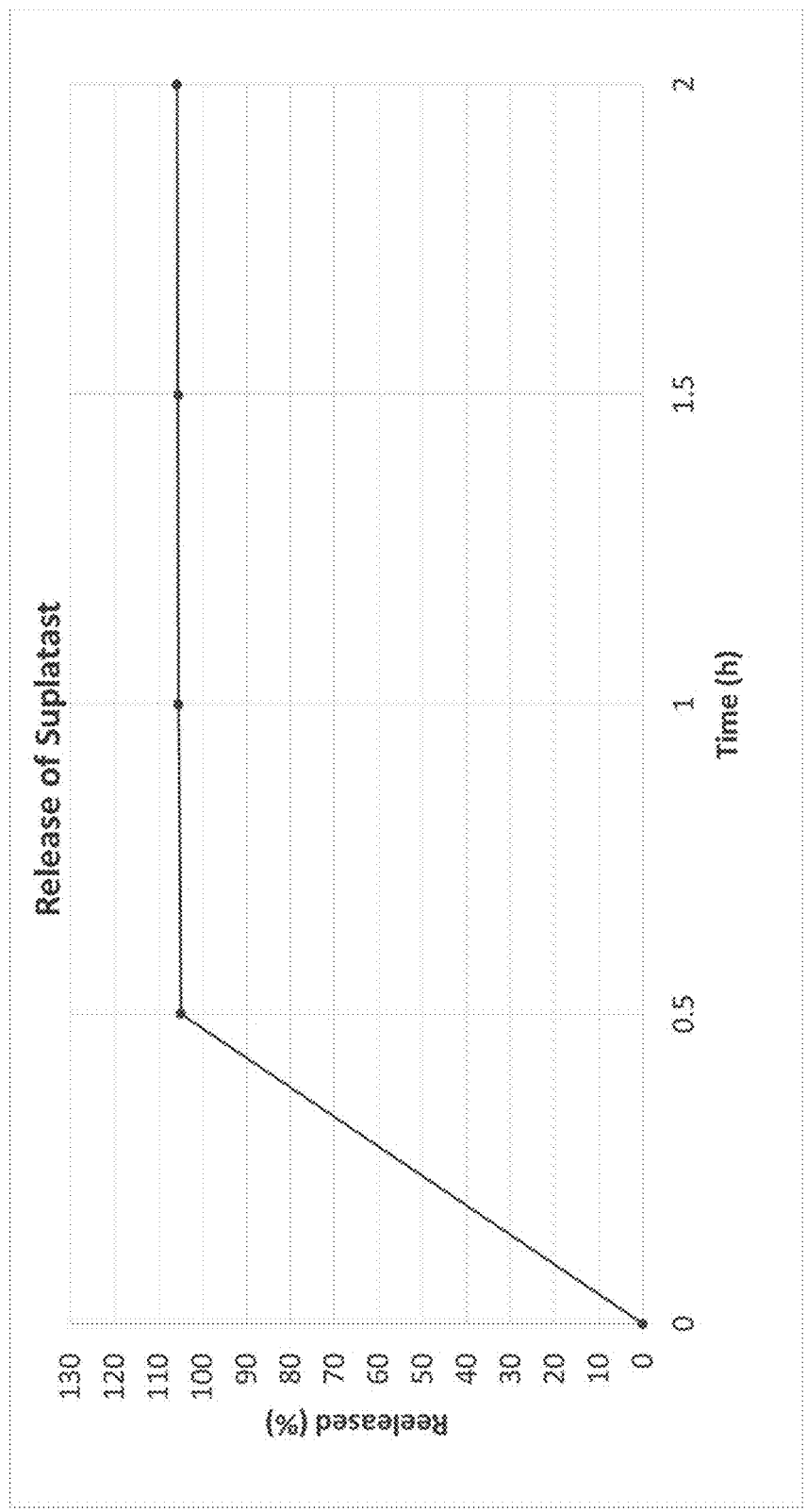

FIG. 6: Release profile of suplatast tosilate mini-tablets coated with hypromellose film—IR (cf. example 11).

Figure 7:
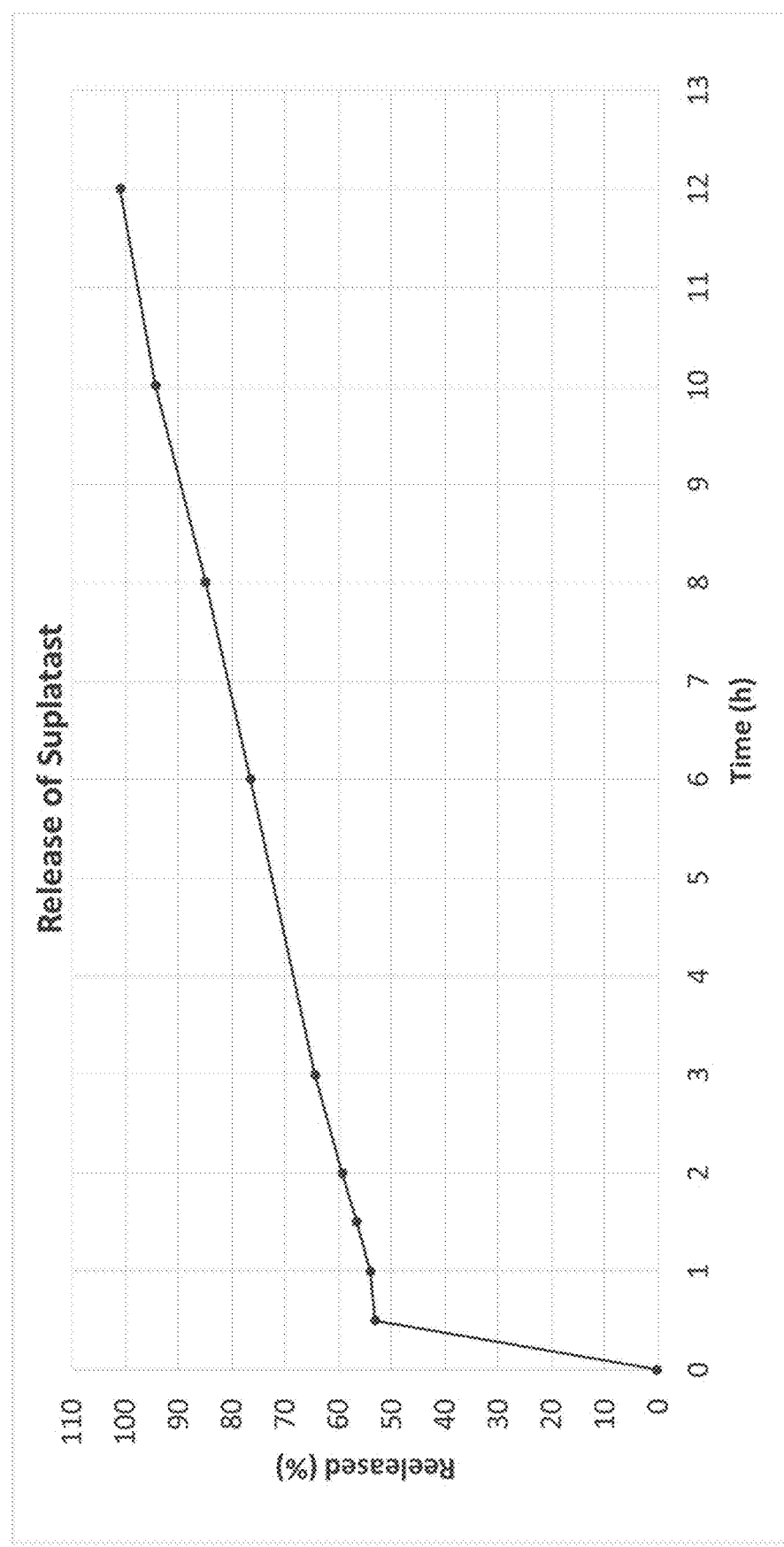

FIG. 7: Release profile of suplatast tosilate mix mini-tablets coated with ethyl cellulose film (ER) or hypromellose film (IR) in capsule (cf. example 12).

Figure 8:
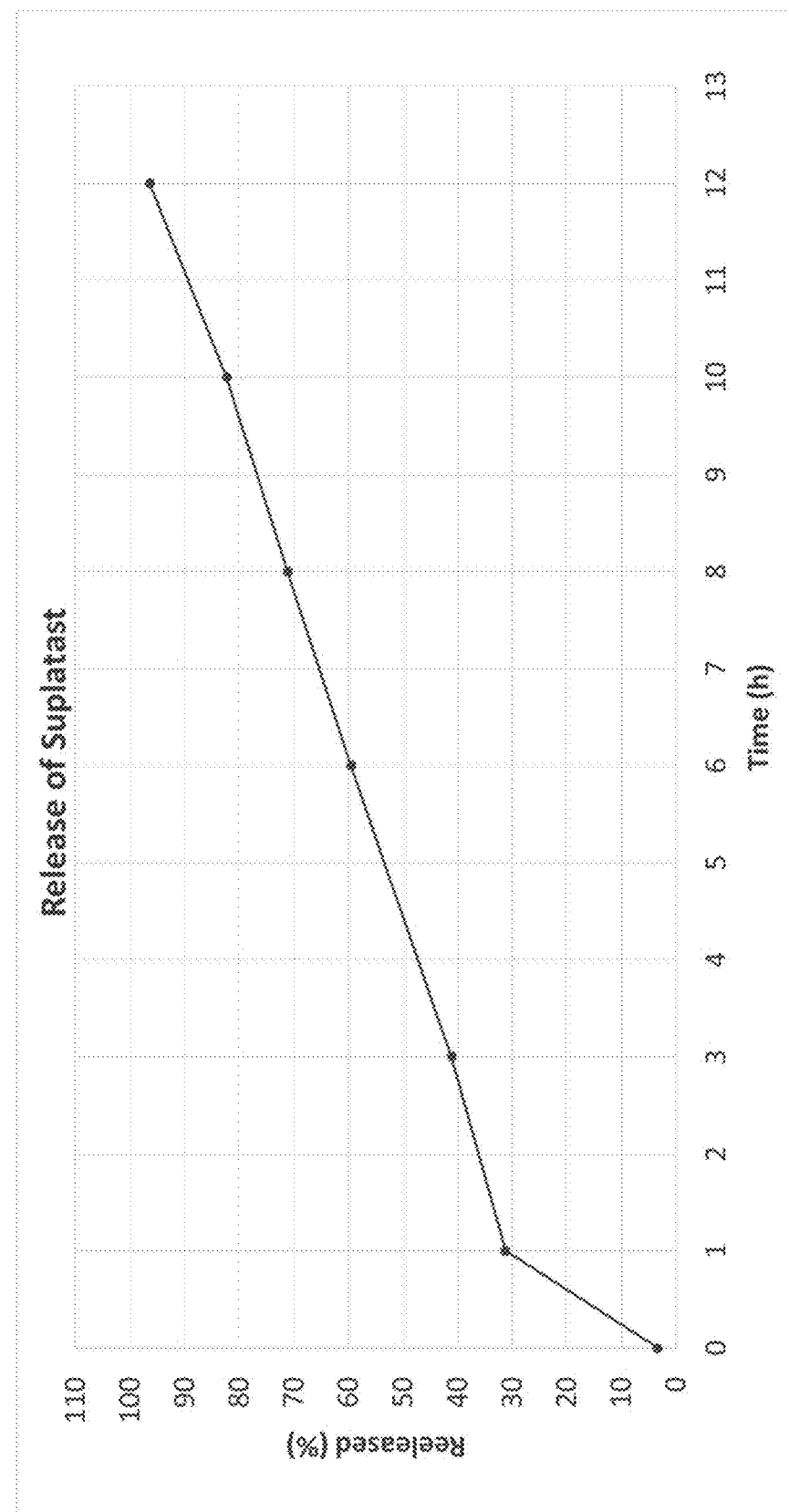

FIG. 8: Release profile of suplatast tosilate barrier coated (ER) and film-coated (IR) tablets (cf. example 13).

Figure 9:
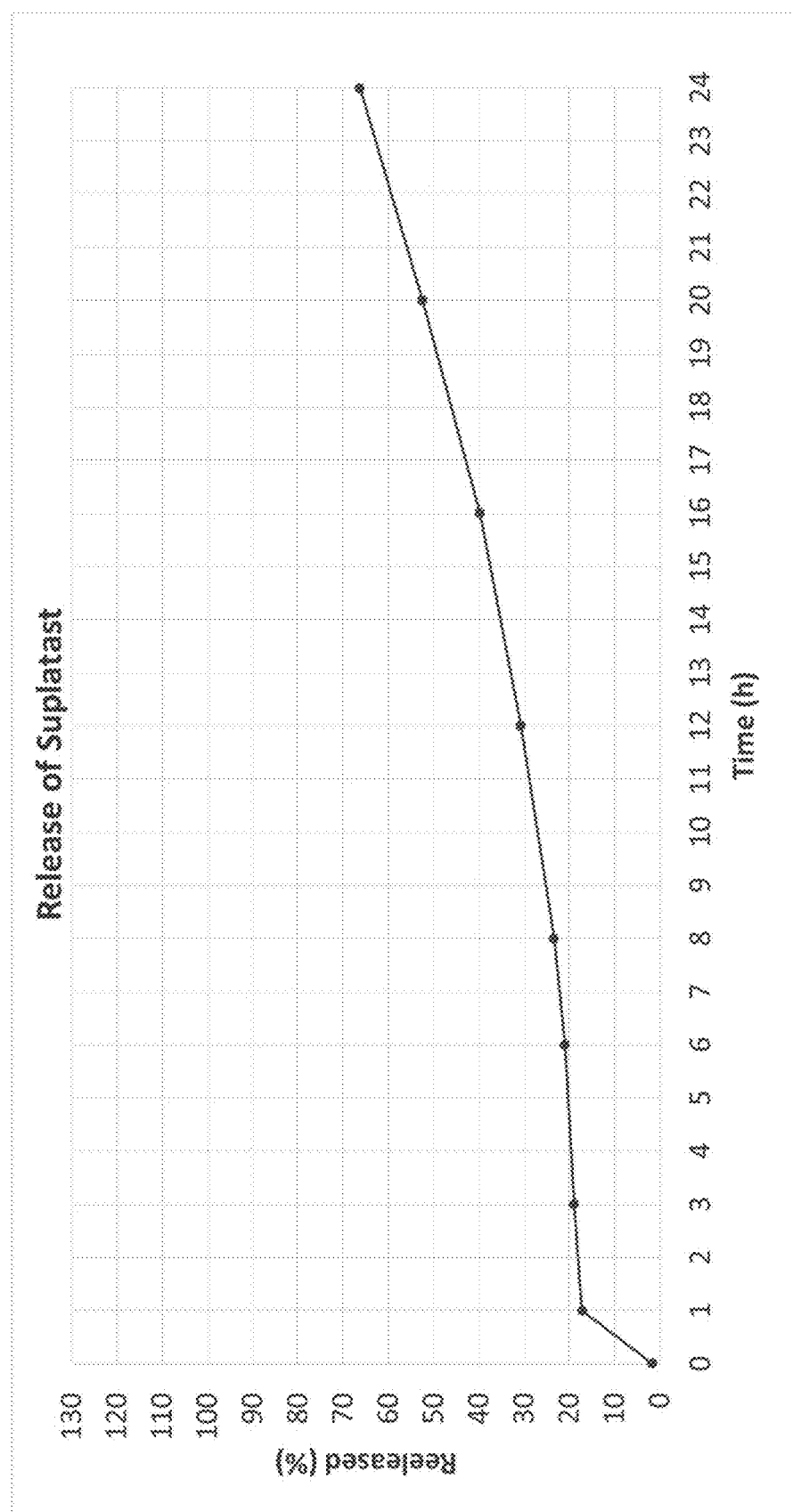

FIG. 9: Release profile of suplatast tosilate barrier coated (ER) and film-coated (IR) tablets (cf. example 14).

Figure 10:
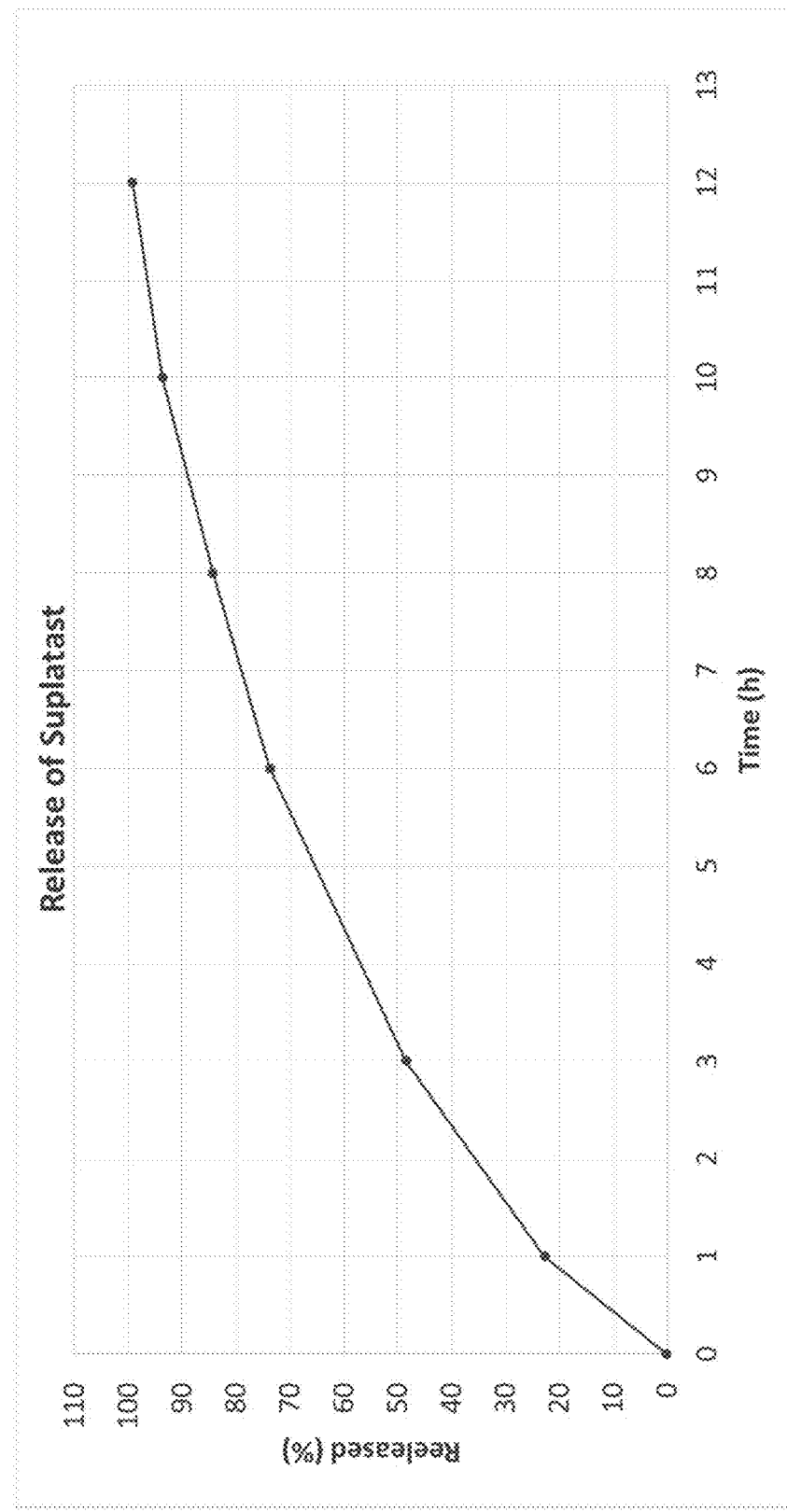

FIG. 10: Release profile of suplatast tosilate bi-layered tablet (IR+ER) (cf. example 15).

DEFINITIONS

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The term "acid addition salt" is intended to include "pharmaceutically acceptable acid addition salt" which indicates salts which are not harmful to the patient. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 66, 2, (1977) which is incorporated herein by reference.

The term "therapeutically effective amount" of a compound as used herein refers to an amount sufficient to cure, alleviate, prevent, reduce the risk of, or partially arrest the clinical manifestations of a given disease or disorder and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

DETAILED DESCRIPTION

Suplatast tosilate (or suplatast tosylate) ((±)-3-{[4-(3-ethoxy-2-hydroxypropoxy)phenyl]amino}-3-oxopropyl)(dimethyl)sulfonium; 4-methylbenzenesulfonate) (abbreviated ST herein) is a drug marketed in Japan for oral treatment of atopic dermatitis, asthma and allergy (rhinitis). It is characterized by its ability to inhibit Th2 cytokine production and by its high degree of safety. It is approved for treatment of children and has during its 20 years on the market only been associated with very few serious adverse effects.

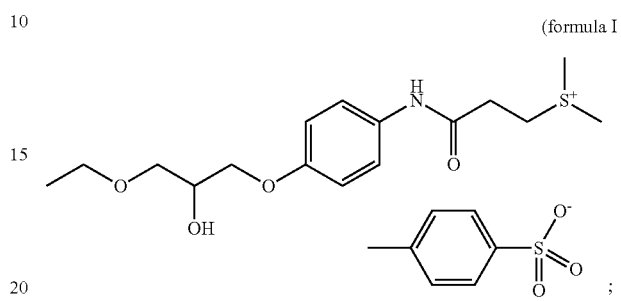

(formula I suplatast tosilate)

Suplatast tosilate is a racemic mixture. There are no significant differences between the two enantiomers with respect to pharmacology (Tada et al: J. Med. Chem. 1998, 41, 3330-3336).

Suplatast tosilate was developed as a derivative of S-methylmethionine in the attempt to identify sulfonium compounds with immunological activities with the ultimate goal to find a suitable clinical candidate for the treatment of allergic disorders (Tada et al: J. Med. Chem. 1998, 41, 3330-3336). The potential therapeutic effects of S-methylmethionine in cytoprotection and wound healing have been described (Kim et al: Pharmacology 2010; 85: 68-76).

In the present context, to achieve the acute effect as well as the sub-chronic effect of the administration of suplatast tosilate, or a pharmaceutically acceptable derivative thereof, said suplatast tosilate is released from a composition with immediate and extended release characteristics.

Provided herein is a special pharmaceutical formulation that is designed to obtain beneficial acute as well as sub-chronic effects of suplatast tosilate, or a pharmaceutically acceptable derivative thereof, in one formulation that can be taken once in the morning for a full-day coverage (constant drug exposure) and/or once in the evening or prior to sleep for a full-night coverage (constant drug exposure).

The disorders which are intended to be treated with the present composition are mainly chronic conditions which require chronic management and thus often life-long medical treatment. Thus, in order to ensure optimal compliance of the patient it is highly advantageous to develop an orally available pharmaceutical formulation, such as a solid dosage form or tablet, which will allow for ease of administration and reduced daily dosages.

Pharmaceutical Composition

The pharmaceutical composition as disclosed herein is formulated for enteral administration, more specifically oral administration.

The present disclosure provides a pharmaceutical composition comprising a compound of formula (I):

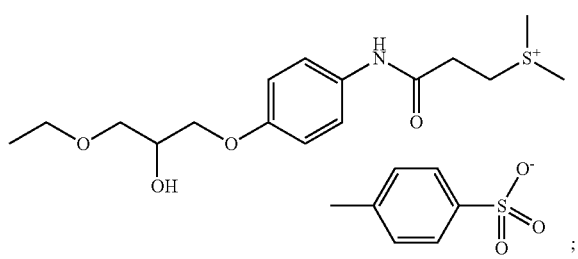

(formula I)

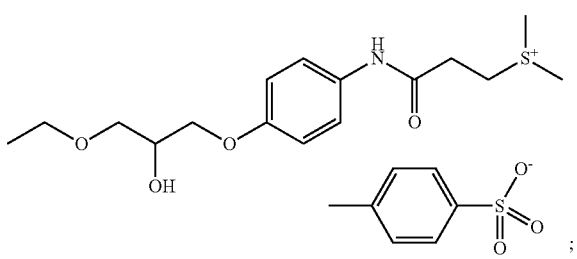

(formula I)

Said compound comprising ((±)-3-{[4-(3-ethoxy-2-hydroxypropoxy)phenyl]amino}-3-oxopropyl)(dimethyl) sulfonium and its counter-ion 4-methylbenzenesulfonate), or a pharmaceutically acceptable derivative thereof.

According to the present disclosure a pharmaceutically acceptable derivative of formula (I), suplatast tosilate, comprises suplatast base ((±)-3-{[4-(3-ethoxy-2-hydroxypropoxy)phenyl]amino}-3-oxopropyl)(dimethyl)sulfonium, and a suitable counter-ion. A counter-ion is the ion that accompanies an ionic species in order to maintain electric neutrality. In one embodiment the counter-ion is a negatively charged counter-ion.

It is an aspect of the present disclosure to provide a pharmaceutical composition comprising a compound of formula (I):

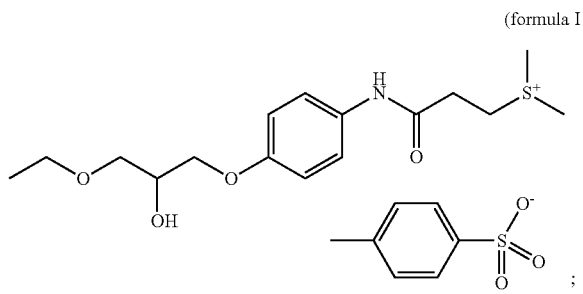

(formula I)

suplatast tosilate), or a pharmaceutically acceptable derivative thereof, said composition comprising, separately or together;

a. a first release component comprising said compound and providing for extended release of said compound, and b. a second release component comprising said compound and providing for immediate release of said compound.

Also disclosed is a pharmaceutical composition comprising, separately or together, a. a first release component comprising suplatast tosilate, or a pharmaceutically acceptable derivative thereof, and providing for extended release thereof, and b. a second release component comprising suplatast tosilate, or a pharmaceutically acceptable derivative thereof, and providing for immediate release thereof.

Also disclosed is a pharmaceutical composition comprising a compound of formula (I):

suplatast tosilate), or a pharmaceutically acceptable derivative thereof, said composition comprising, separately or together;

a. an extended release component comprising said compound, and b. an immediate release component comprising said compound.

Also disclosed is a pharmaceutical composition comprising, separately or together, a. an extended release component suplatast tosilate, or a pharmaceutically acceptable derivative thereof, and b. an immediate release component comprising suplatast tosilate, or a pharmaceutically acceptable derivative thereof.

In one embodiment the composition as defined herein comprises the racemic compound of suplatast tosilate.

In one embodiment the composition as defined herein comprises or consists of the (+)-suplatast tosilate enantiomer. In one embodiment the composition as defined herein comprises or consists of the (−)-suplatast tosilate enantiomer. In one embodiment the composition as defined herein comprises the (+)-suplatast tosilate enantiomer and the (−)-suplatast tosilate enantiomer.

The present pharmaceutical composition thus comprises two components; the first release component a. (or the extended release component a.) and the second release component b. (or the immediate release component b.), each component comprising the same active pharmaceutical ingredient (API); suplatast tosilate or a pharmaceutically acceptable derivative thereof.

The present pharmaceutical composition is thus designed to release the active pharmaceutical ingredient differently; the first release component providing for extended release of suplatast tosilate or a pharmaceutically acceptable derivative thereof, and the second release component providing for immediate release of suplatast tosilate or a pharmaceutically acceptable derivative thereof.

In one embodiment immediate release from the second release component occurs first, followed by, and optionally overlapping with, extended release from the first release component.

In one embodiment immediate release from the second release component and extended release from the first release component occurs simultaneously.

In one embodiment extended release from the first release component occurs first, followed by, and optionally overlapping with, immediate release from the second release component.

Time- or controlled release technology (extended or sustained release) is a mechanism used in pill tablets or capsules to dissolve slowly and release a drug over time. The advantages of extended-release tablets or capsules are that they may be taken less frequently than immediate-release formulations, and that they keep steadier levels of the drug in the bloodstream.

Controlled-release drugs may be formulated so that the active pharmaceutical ingredient is embedded in a matrix of insoluble substance(s) such that the dissolving drug must find its way out through the holes in the matrix. Some drugs are enclosed in polymer-based tablets with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some formulations, the drug dissolves into the matrix, and the matrix physically swells to form a gel, allowing the drug to exit through the gel's outer surface. Micro-encapsulation also produces complex dissolution profiles; through coating an active pharmaceutical ingredient around an inert core and layering it with insoluble substances to form a microsphere a more consistent and replicable dissolution rate is obtained—in a convenient format that may be mixed with other instant release pharmaceutical ingredients, e.g. into any two piece gelatin capsule.

Dosage forms are a mixture of active drug components and nondrug components. The pharmaceutical composition as disclosed herein is in one embodiment a pharmaceutical dosage form, such as an oral dosage form. In a particular embodiment, said dosage form is a solid dosage form, a solid oral dosage form, such as a tablet or mini-tablet.

Solid dosage forms (or solid form preparations) include powders, tablets (including mini-tablets and micro-tablets), pills, capsules, spheres, pellets, cachets, suppositories, and dispersible granules.

According to the present disclosure, in the same solid dosage form the active pharmaceutical ingredient is in one embodiment combined so as to provide controlled release and immediate release of said active pharmaceutical ingredient.

A tablet is a pharmaceutical dosage form comprising a mixture of active substances and excipients, pressed or compacted into a solid dose. Tablets are simple and convenient to use. They provide an accurately measured dosage of the active ingredient in a convenient portable package. Manufacturing processes and techniques can provide tablets special properties, for example, extended release or fast dissolving formulations.

Mini-tablets are tablets with a diameter≤3 mm and represent a new trend in solid dosage form design, with the main goal of overcoming some therapeutic obstacles such as impaired swallowing and polypharmacy therapy, and also offering some therapeutic benefits such as dose flexibility and combined release patterns.

In one embodiment a mini-tablet according to the disclosure is a tablet with a diameter less than or equal to (≤) 3 mm, such as ≤2.5 mm, for example ≤2 mm, such as ≤1.5 mm, for example about 1 mm. In one embodiment a mini-tablet according to the present disclosure is a tablet with a diameter of 1 to 1.5 mm, such as 1.5 to 2 mm, for example 2 to 2.5 mm, such as 2.5 to 3 mm.

In the manufacture of pharmaceuticals, encapsulation refers to a range of dosage forms in a relatively stable shell known as a capsule, allowing them to, for example, be taken orally or be used as suppositories. There are two main types of capsules: Hard-shelled capsules made in two halves: a lower-diameter "body" that is filled and then sealed using a higher-diameter "cape"; and soft-shelled capsules, primarily used for oils and for active ingredients that are dissolved or suspended in oil. Both types of capsules are made from aqueous solutions of gelling agents including animal protein mainly gelatin and plant polysaccharides or their derivatives like carrageenans and modified forms of starch and cellulose. Other ingredients can be added to the gelling agent solution like plasticizers such as glycerin and/or sorbitol to decrease the capsule's hardness, coloring agents, preservatives, disintegrants, lubricants and surface treatment.

In one embodiment the first release component and/or the second release component are in a dosage form selected from the group consisting of a tablet, a mini-tablet, a micro-tablet, a sphere, a pellet, a granule and a capsule.

In one embodiment the first release component and/or the second release component are in a dosage form selected from the group consisting of a coated tablet, a coated mini-tablet, a coated micro-tablet, a coated sphere, a coated pellet, a coated granule and a coated capsule.

As detailed elsewhere, the pharmaceutical composition or dosage form as disclosed herein comprises, separately or together;
  a. a first release component comprising suplatast tosilate, or a pharmaceutically acceptable derivative thereof, and providing for extended release thereof, and
  b. a second release component comprising suplatast tosilate, or a pharmaceutically acceptable derivative thereof, and providing for immediate release thereof.

The first release component a. is formulated to release the active ingredient by a controlled release procedure or rate, namely by extended release, while the second release component b. is formulated for immediate release of the active ingredient.

In one embodiment the composition as disclosed herein comprises the first release component and the second release component in separate compartments, parts or layers.

In one embodiment the composition as disclosed herein comprises
  a. a first release component which is an inner core providing for extended release of suplatast tosilate, or a pharmaceutically acceptable derivative thereof, and
  b. a second release component which is an outer coating or layer providing for immediate release of suplatast tosilate, or a pharmaceutically acceptable derivative thereof,
wherein said second release component outer coating or layer is applied onto the first release component inner core.

In one embodiment the composition as disclosed herein comprises
  a. a first release component which is a tablet, a mini-tablet, a sphere, a pellet or a granule, optionally coated, providing for extended release of suplatast tosilate, or a pharmaceutically acceptable derivative thereof, and
  b. a second release component, which is an outer coating or layer on said tablet, mini-tablet, sphere, pellet or granule, said outer coating or layer providing for immediate release of suplatast tosilate, or a pharmaceutically acceptable derivative thereof.

In one embodiment the composition as disclosed herein comprises
  a. a first release component which is a film-coated tablet, a film-coated mini-tablet or a film-coated sphere providing for extended release of suplatast tosilate, or a pharmaceutically acceptable derivative thereof, and
  b. a second release component, which is an outer coating or layer on said film-coated tablet, film-coated mini-tablet or a film-coated sphere, providing for immediate release of suplatast tosilate, or a pharmaceutically acceptable derivative thereof.

In one embodiment, the first release component a. is an extended-release tablet such as an extended-release mini-tablet, optionally comprising a coating, and the second release component b. is an immediate-release outer coating or layer applied to said tablet.

In one embodiment the composition as disclosed herein comprises
a. a first release component which is an outer coating or layer providing for extended release of suplatast tosilate, or a pharmaceutically acceptable derivative thereof, and
b. a second release component which is an inner core providing for immediate release of suplatast tosilate, or a pharmaceutically acceptable derivative thereof,
wherein said first release component outer coating or layer is applied onto the second release component inner core.

In one embodiment, the first release component a. is a component in a bi-layered dosage form or tablet, and the second release component b. is another component in the same bi-layered dosage form or tablet.

In one embodiment the composition as disclosed herein is a bi-layered tablet (or mini-tablet) comprising
a. a first release layer providing for extended release of suplatast tosilate, or a pharmaceutically acceptable derivative thereof, and
b. a second release layer providing for immediate release of suplatast tosilate, or a pharmaceutically acceptable derivative thereof,
wherein each layer is present within the same tablet.

In one embodiment, the first release component a. and/or the second release component b. are each mini-tablets, which mini-tablets are filled into capsules.

In one embodiment, the first release component a. are immediate-release mini-tablets and the second release component b. are extended-release mini-tablets, which mini-tablets a. and b. are mixed and filled into capsules.

In one embodiment the composition as disclosed herein is a multiparticulate dosage form comprising, separately or together, two or more dosage forms.

In one embodiment the composition as disclosed herein comprises
a. a first release component which is one or more extended-release tablets, mini-tablets, granules or pellets comprising suplatast tosilate, or a pharmaceutically acceptable derivative thereof, and
b. a second release component which is one or more immediate-release tablets, mini-tablets, granules or pellets comprising suplatast tosilate, or a pharmaceutically acceptable derivative thereof.

In one embodiment the composition as disclosed herein comprises
a. a first release component which is one or more extended-release tablets or mini-tablets comprising a semi-permeable film, and
b. a second release component which is one or more immediate-release tablets or mini-tablets comprising a soluble film.

In one embodiment the composition as disclosed herein comprises
a. a first release component which is a plurality of extended-release tablets, mini-tablets, granules or pellets, and
b. a second release component which is a plurality of immediate-release tablets, mini-tablets, granules or pellets,
wherein said first and second release components are provided together in an appropriate container such as a capsule, a pouch a sachet or a stick pack.

In one embodiment the composition as disclosed herein comprises
a. a first release component which is a plurality of extended-release tablets, mini-tablets, granules or pellets, and
b. a second release component which is a plurality of immediate-release tablets, mini-tablets, granules or pellets,
wherein said first release component is provided in an appropriate container such as a capsule, a pouch a sachet or a stick pack, and said second release component is provided in an appropriate container such as a capsule, a pouch a sachet or a stick pack.

Pharmaceutical Composition—Excipients

The pharmaceutical composition according to the present disclosure comprises the active pharmaceutical ingredient (API) as detailed herein elsewhere, as well as one or more excipients.

An excipient is a pharmacologically inactive substance formulated with the active ingredient (API) of a medication. Excipients are commonly used to bulk up formulations that contain active ingredients to allow convenient and accurate dispensation of a drug substance when producing a dosage form.

In one embodiment, the pharmaceutical composition as disclosed herein comprises one or more excipients. Said one or more excipients may act as a solid carrier, diluent, flavouring agent, solubilizer, lubricant, glidants, suspending agent, binder, filler, preservative, antiadherent, wetting agent, swelling agent, tablet disintegrating agent, sorbent, and/or an encapsulating/coating material.

The present pharmaceutical composition comprises at least one excipient in order to obtain a suitable formulation such as a dosage form for oral administration with the ER (extended release) and IR (immediate release) characteristics, respectively, as desired.

In one embodiment the first and second release components each comprises one or more release-controlling excipients.

First Release Component—Extended Release

In one embodiment, the first release component of the presently disclosed pharmaceutical composition comprises suplatast tosilate, or a pharmaceutically acceptable derivative thereof, and one or more release-controlling excipients, and optionally one or more further excipients such as swelling agents, fillers, binders and lubricants.

In one embodiment said first release component comprises one or more release-controlling excipients providing for extended release.

Release-controlling excipients may be any release controlling excipient known to the skilled person. In one embodiment, the first release component comprises one or more release controlling excipients selected from the group consisting of hydroxypropylmethylcellulose (HPMC, hypromellose), methylcellulose, hydroxypropyl cellulose, hypromellose acetate succinate, hypromellose phthalate, cellulose acetate, glycerin monostearate, glyceryl monooleate, glyceryl palmitate, glyceryl behenate, hydrogenated vegetable oil, guar gum, polyvinyl alcohol, alginates, xanthan gum, carnauba wax, yellow wax, white wax, zein, carregeenan, carbomers and agar.

In one embodiment the first release component comprises a swelling agent, such as a non-ionic or ionic swelling agent, such as a swelling agent selected from the group consisting of Low-Substituted Hydroxypropyl Cellulose (L-HPC), HPC, alginic acid, calcium alginate, sodium alginate, carboxymethylcellulose calcium, carboxymethylcellulose sodium, croscarmellose sodium, crospovidone, guar gum, hydroxypropyl cellulose, magnesium aluminum silicate, methylcellulose, microcrystalline cellulose (MCC), polacrilin potassium, povidone, sodium starch glycolate starch or pregelatinized starch.

In one embodiment the first release component comprises a filler, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment the first release component comprises a binder, such as a binder selected from the group consisting of acacia, alginic acid, carbomers, carboxymethylcellulose sodium, carrageenan, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose, hydroxypropyl starch, hypromellose, methylcellulose, poloxamer, polydextrose, polyethylene oxide, povidone, sodium alginate, sucrose, starch, pregelatinized starch and maltodextrin.

In one embodiment the first release component comprises a lubricant, such as a lubricant selected from the group consisting of calcium stearate, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, sodium lauryl sulfate, stearic acid, talc, silica, stearic acid and zinc stearate.

Any other excipients suitable for the purpose of the present disclosure and known to the skilled person are considered encompassed herewith.

Hydroxypropylmethylcellulose (HPMC), also known as hypromellose, is used as an excipient in oral tablet and capsule formulations, where, depending on the grade, it functions as a controlled release agent or release-controlling excipient to delay the release of a medicinal compound into the digestive tract. It is also used as a binder and as a component of tablet coatings.

Different grades of HPMC have different characteristics with respect to e.g. viscosity. Thus, different HPMCs will have different impacts on the release rates of the embedded API. Also, the amount of HPMC in the formulation, the hardness or degree of compression of the formulation into a tablet, as well as any potential coatings, will potentially impact the release rates of the API. The release rates may be determined by evaluating the dissolution profiles of the produced granules or batches. In vitro drug dissolution data generated from dissolution testing experiments can be related to in vivo pharmacokinetic data by means of in vitro-in vivo correlations (IVIVC). Several dissolution apparatuses exist.

An Extended-Release Tablet or Mini-Tablet Comprising ST:

In one embodiment the first release component a. is a film-coated tablet or mini-tablet with extended-release properties. Examples of such are provided in Examples 1, 2, 10 and 12-14.

In one embodiment the first release component a. is a film-coated tablet or film-coated mini-tablet comprising one or more of
  suplatast tosilate,
  microcrystalline cellulose,
  L-HPC,
  a croscarmellose, and
  magnesium stearate,
wherein the film-coating comprises a semi-permeable film based on ethylcellulose (ethylcellulose and ethanol).

In one embodiment the first release component a. is a film-coated tablet or film-coated mini-tablet comprising one or more of
  suplatast tosilate,
  microcrystalline cellulose,
  Sodium starch glycolate (type A),
  pre-gelatinized starch,
  citric acid monohydrate, and
  magnesium stearate,
wherein the film-coating comprises a semi-permeable film based on ethylcellulose (ethylcellulose, hypromellose and ethanol).

The extended-release tablet or mini-tablet will be dosed with an immediate-release dosage form, according to the present disclosure.

Second Release Component—Immediate Release

In one embodiment, the second release component of the presently disclosed pharmaceutical composition comprises suplatast tosilate, or a pharmaceutically acceptable derivative thereof, and one or more excipients, one or more film-forming excipients, binders, fillers, disintegrants or lubricants.

A film-forming excipient may be any film-forming excipient known to the skilled person. In one embodiment, the second release component comprises one or more film-forming excipient selected from the group consisting of hydroxypropylmethylcellulose (HPMC), methylcellulose, hydroxyethyl cellulose, hydroxypropyl cellulose, hypromellose acetate succinate, hypromellose phthalate, chitosan, copovidone, ethylcellulose, gelatin, cellulose acetate, polymethacrylates, polyvinyl alcohol and alginates.

In one embodiment the second release component comprises a filler, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment the second release component comprises a binder, such as a binder selected from the group consisting of acacia, alginic acid, carbomers, carboxymethylcellulose sodium, carrageenan, cellulose, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose (HPC), hydroxypropyl starch, hypromellose, methylcellulose, poloxamer, polydextrose, polyethylene oxide, povidone, sodium alginate, starch, pregelatinized starch, maltodextrin and synthetic polymers such as PVP (polyvinylpyrrolidone) and PEG (polyethylene glycol).

In one embodiment the second release component comprises a disintegrant, such as a disintegrant selected from the group consisting of Low-Substituted Hydroxypropyl Cellulose (L-HPC), HPC, alginic acid, calcium alginate, sodium alginate, carboxymethylcellulose calcium, carboxymethylcellulose sodium, croscarmellose sodium, crospovidone, guar gum, hydroxypropyl cellulose, magnesium aluminum silicate, methylcellulose, microcrystalline cellulose (MCC), polacrilin potassium, povidone, sodium starch glycolate starch or pregelatinized starch.

In one embodiment the second release component comprises a lubricant, such as a lubricant selected from the group consisting of calcium stearate, cooloidal silicon dioxide, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, silicon dioxide, sodium lauryl sulfate, stearic acid, talc and zinc stearate.

In one embodiment the second release component is a coating, such as a coating on an inner core, inner matrix, a tablet or a mini-tablet comprising the first release component. Said coating may be applied by coating or spraying of any kind known to the skilled person.

The second release component may also in one embodiment be in the form of a matrix, such as a solid matrix, tablet or mini-tablet having immediate release characteristics. Such formulations are known to the skilled person.

An Immediate-Release Tablet or Mini-Tablet Comprising ST:

In one embodiment the second release component b. is a film-coated mini-tablet with immediate-release properties. An example of such is provided in Example 3 and 11-13.

In one embodiment the second release component b. is a film-coated tablet or film-coated mini-tablet comprising
 suplatast tosilate,
 microcrystalline cellulose
 L-HPC
 a croscarmellose
 magnesium stearate,
wherein the film-coating comprises a soluble film based on hypromellose (hypromellose and polyethylene glycol).

The immediate-release mini-tablet will be dosaged with an extended-release dosage form, according to the present disclosure.

Pharmaceutical Composition Comprising the First and the Second Release Components In one embodiment the first release component a. is a semi-permeable film-coated mini-tablet or tablet with extended-release properties and the second release component b. is a soluble film-coated mini-tablet or tablet with immediate-release properties; which mini-tablets are mixed and combined e.g. in a capsule. Examples of such are provided in Examples 4, 5, and 12.

In one embodiment the composition as disclosed herein comprises
 a. a first release component which is a film-coated tablet or film-coated mini-tablet comprising one or more of
  suplatast tosilate,
  microcrystalline cellulose,
  sodium starch glycolate (type A),
  pre-gelatinized starch,
  citric acid monohydrate, and
  magnesium stearate,
  wherein the film-coating comprises a semi-permeable film based on ethylcellulose (ethylcellulose, hypromellose and ethanol), and
 b. a second release component which is a film-coated tablet or film-coated mini-tablet comprising one or more of
  suplatast tosilate,
  microcrystalline cellulose,
  L-HPC,
  a croscarmellose and
  magnesium stearate,
  wherein the film-coating comprises a soluble film based on hypromellose (hypromellose and polyethylene glycol),
wherein said first and second release components are provided together in an appropriate container such as a capsule, a pouch a sachet or a stick pack; or wherein said first release component is provided in an appropriate container such as a capsule, a pouch a sachet or a stick pack, and said second release component is provided in an appropriate container such as a capsule, a pouch a sachet or a stick pack.

In one embodiment the composition as disclosed herein comprises
 a. a first release component which is a film-coated tablet or film-coated mini-tablet comprising one or more of
  suplatast tosilate,
  microcrystalline cellulose,
  L-HPC,
  a croscarmellose and
  magnesium stearate,
  wherein the film-coating comprises a semi-permeable film based on ethylcellulose (ethylcellulose and ethanol), and
 b. a second release component which is a film-coated tablet or film-coated mini-tablet comprising one or more of
  suplatast tosilate,
  microcrystalline cellulose
  L-HPC
  a croscarmellose
  magnesium stearate,
  wherein the film-coating comprises a soluble film based on hypromellose (hypromellose and polyethylene glycol),
wherein said first and second release components are provided together in an appropriate container such as a capsule, a pouch a sachet or a stick pack; or wherein said first release component is provided in an appropriate container such as a capsule, a pouch a sachet or a stick pack, and said second release component is provided in an appropriate container such as a capsule, a pouch a sachet or a stick pack.

In one embodiment the first release component a. is a tablet with extended-release properties and the second release component b. is a coating with immediate-release properties. Examples of such are provided in Examples 6, 7, 9, 13 and 14.

In one embodiment the composition as disclosed herein comprises
 a. a first release component which is a film-coated tablet providing for extended release of suplatast tosilate, said tablet comprising one or more of
  suplatast tosilate,
  hypromellose 4000,
  optionally microcrystalline cellulose and citric acid monohydrate,
  silicon dioxide and,
  magnesium stearate,
  wherein the film-coating comprises a semi-permeable barrier film based on ethyl cellulose, said film coating comprising one or more of ethyl cellulose 7 cps, ethanol 96% and hypromellose 3 cps, and
 b. a second release component, which is an immediate release film containing suplatast tosilate applied onto said coated tablet, said film comprising
  suplatast tosilate,
  polyethylene glycol, and
  hypromellose 15 cps.

In one embodiment the composition as disclosed herein comprises
- a. a first release component which is a film-coated tablet providing for extended release of suplatast tosilate, said tablet comprising one or more of
  - suplatast tosilate,
  - hypromellose 4000,
  - microcrystalline cellulose
  - citric acid monohydrate,
  - silicon dioxide and,
  - magnesium stearate,
  - wherein the film-coating comprises a semi-permeable barrier film based on ethyl cellulose, said film coating comprising one or more of ethyl cellulose 7 cps, ethanol 96% and hypromellose 3 cps, and
- b. a second release component, which is an immediate release film coating containing suplatast tosilate applied onto said coated tablet, said film comprising
  - suplatast tosilate,
  - polyethylene glycol, and
  - hypromellose 15 cps.

In one embodiment the composition as disclosed herein comprises
- a. a first release component which is a tablet providing for extended release of suplatast tosilate, said tablet comprising one or more of
  - suplatast tosilate,
  - hypromellose 4000,
  - microcrystalline cellulose,
  - sodium carboxymethylcellulose and
  - magnesium stearate; and
- b. a second release component, which is an immediate release coating containing suplatast tosilate applied on said tablet, said film comprising
  - suplatast tosilate,
  - hypromellose 4000,
  - microcrystalline cellulose,
  - lactose,
  - croscarmellose and
  - magnesium stearate, wherein the second release component is applied as a compression coating (press coating) on the first release component tablet.

In one embodiment the first release component a. is an extended-release layer of a bi-layer tablet, and the second release component b. is an immediate-release layer of a bi-layer tablet. An example of such is provided in Example 8 and 15.

In one embodiment the composition as disclosed herein is a bi-layered tablet (or mini-tablet) comprising
- a. a first release layer providing for extended release of suplatast tosilate, or a pharmaceutically acceptable derivative thereof, said layer comprising one or more of
  - suplatast tosilate,
  - hypromellose 4000,
  - microcrystalline cellulose,
  - citric acid monohydrate,
  - sodium carboxymethylcellulose and
  - magnesium stearate,
- b. a second release layer providing for immediate release of suplatast tosilate, or a pharmaceutically acceptable derivative thereof, said layer comprising one or more of
  - suplatast tosilate,
  - hypromellose 4000,
  - microcrystalline cellulose,
  - citric acid monohydrate,
  - lactose,
  - croscarmellose and
  - magnesium stearate, wherein the first release layer is compressed as layer 1 and the second release layer is compressed as layer 2 on a bi-layer tablet press to provide a bi-layered tablet.

Pharmaceutical Composition—Further Active Ingredient

The pharmaceutical composition according to the present disclosure comprises the active pharmaceutical ingredient (API) as detailed herein elsewhere, and in one embodiment one or more further active ingredients.

In one embodiment there is provided a pharmaceutical composition comprising suplatast tosilate, or a pharmaceutically acceptable derivative thereof, said composition comprising, separately or together;
- a. a first release component comprising said compound and providing for extended release of said compound, and
- b. a second release component comprising said compound and providing for immediate release of said compound, wherein said composition further comprises, separately or together, one or more further active pharmaceutical ingredients.

Administration and Dosage

According to the present disclosure, the composition comprising a compound of formula (I) is administered to individuals in need of treatment in pharmaceutically effective doses. A therapeutically effective amount of a compound is an amount sufficient to cure, prevent, reduce the risk of, alleviate or partially arrest the clinical manifestations of a given disease and its complications. The amount that is effective for a particular therapeutic purpose will depend on the severity and the sort of the disorder as well as on the weight and general state of the subject.

The composition according to the present disclosure may be administered one or several times per day, such as from 1 to 4 times per day, such as from 1 to 3 times per day, such as from 1 to 2 times per day, such as from 2 to 4 times per day, such as from 2 to 3 times per day. Alternatively, the compounds may be administered less than once a day, for example once a day, such as once every second day, for example once every third day, such as once every fourth day, for example once every fifth day, such as once every sixth day, for example once every week.

In one embodiment the present composition is administered once in the morning and/or once in the evening or prior to sleep. In one embodiment the present composition is administered once in the morning and once in the evening or prior to sleep. In one embodiment the present composition is administered once in the morning. In one embodiment the present composition is administered once in the evening or prior to sleep.

In one embodiment the present composition is administered as required or as needed, in addition to the once in the morning and/or once in the evening or prior to sleep administration, to alleviate acute symptoms of disease.

Administration may occur for a limited time, or administration may be chronic, the treatment may be chronic from the onset of diagnosis, such as throughout the lifetime of the individual or as long as the individual will benefit therefrom. The composition may be administered to an individual at various time points of treatment. The treatment may be done over one continued period, or in intervals with periods in between wherein the administration is stopped, decreased or altered.

The concentration of the active pharmaceutical ingredient in the present pharmaceutical composition is optimized to achieve an appropriate dosage thereof. The concentration of the active pharmaceutical ingredients in the first release component and the second release component may be the same or different.

In one embodiment the concentration or dosage of suplatast tosilate, or a pharmaceutically acceptable derivative thereof, is essentially the same in the first and the second release component.

In one embodiment the concentration or dosage of suplatast tosilate, or a pharmaceutically acceptable derivative thereof, is different in the first and in the second release component; such as a higher concentration or dosage in the first release component or a higher concentration or dosage in the second release component.

In one embodiment the concentration of suplatast tosilate, or a pharmaceutically acceptable derivative thereof, is higher in the first release component (ER) than in the the second release component (IR).

In one embodiment the concentration or dosage of suplatast tosilate, or a pharmaceutically acceptable derivative thereof, is 1-10 times higher in the first release component (ER) than in the second release component (IR),
such as 1 time higher, 2 times higher, 3 times higher, 4 times higher, 5 times higher, 6 times higher, 7 times higher, 8 times higher, 9 times higher or 10 times higher in the first release component (ER); or
such as 1-2 times higher, 2-3 times higher, 3-4 times higher, 4-5 times higher, 5-6 times higher, 6-7 times higher, 7-8 times higher, 8-9 times higher, 9-10 times higher in the first release component (ER).

In one embodiment the concentration or dosage ratio of suplatast tosilate, or a pharmaceutically acceptable derivative thereof, of the first release component (ER) and the second release component (IR) is 10:1 to 1:1, such as 10:1, 9:1, 8:1, 7:1, 6:1, 5:1, 4:1, 3:1, 2:1 or 1:1.

In one embodiment the concentration or dosage ratio of suplatast tosilate, or a pharmaceutically acceptable derivative thereof, of the first release component (ER) and the second release component (IR) is 10:1 to 9:1, 9:1 to 8:1, 8:1 to 7:1, 7:1 to 6:1, 6:1 to 5:1, 5:1 to 4:1, 4:1 to 3:1, 3:1 to 2:1 or 2:1 to 1:1.

In one embodiment the first release component (ER) and the second release component (IR) each comprises a dosage of 25 to 1000 mg or 50 to 1000 mg suplatast tosilate, or a pharmaceutically acceptable derivative thereof, per component, such as 25-50 mg, 50-100 mg, 100-200 mg, 200-250 mg, 250-300 mg, 300-400 mg, 400-500 mg, 500-600 mg, 600-700 mg, 700-800 mg, 800-900 mg, such as 900-1000 mg per component.

In one embodiment the first release component (ER) comprises a dosage of 50-500 mg suplatast tosilate, or a pharmaceutically acceptable derivative thereof, such as 50-100 mg, 100-150 mg, 150-200 mg, 200-250 mg, 250-300 mg, 300-350 mg, 350-400 mg, 400-450 mg, 450-500 mg; such as 50 mg, 100 mg, 150 mg, 200 mg, 250 mg, 300 mg, 350 mg, 400 mg, 450 mg, 500 mg suplatast tosilate, or a pharmaceutically acceptable derivative thereof;
and the second release component (IR) comprises a dosage of 25-250 mg suplatast tosilate, or a pharmaceutically acceptable derivative thereof, such as 25-50 mg, 50-75 mg, 75-100 m, 100-150 mg, 150-200 mg, 200-250 mg; such as 25 mg, 50 mg, 75 mg, 100 mg, 150 mg, 200 mg, 250 mg suplatast tosilate, or a pharmaceutically acceptable derivative thereof.

In one embodiment the first release component (ER) comprises a dosage of 100-500 mg suplatast tosilate, or a pharmaceutically acceptable derivative thereof, and the second release component (IR) comprises a dosage of 50-100 mg suplatast tosilate, or a pharmaceutically acceptable derivative thereof.

In one embodiment the first release component (ER) comprises a dosage of 150-750 mg suplatast tosilate, or a pharmaceutically acceptable derivative thereof, and the second release component (IR) comprises a dosage of 75-150 mg suplatast tosilate, or a pharmaceutically acceptable derivative thereof.

In one embodiment the first release component (ER) comprises a dosage of 100-250 mg suplatast tosilate, or a pharmaceutically acceptable derivative thereof, and the second release component (IR) comprises a dosage of 50-100 mg suplatast tosilate, or a pharmaceutically acceptable derivative thereof.

In one embodiment the concentrations or dosages are administered once a day (QD), twice a day (BID), three times a day (TID) and/or four times a day (QID). In a preferred embodiment the dosage is given in one dosage once a day (QD) or one dosage twice a day (BID).

In one embodiment the composition comprising a compound of formula (I) as defined herein is administered in a therapeutically effective amount, such as in an amount of 0.1 mg to 5000 mg compound of formula (I) (calculated as the free base) per day; such as in an amount of 1 mg to 1000 mg compound per day.

It follows that in one embodiment the compound is administered in an amount of 0.1 mg to 1 mg suplatast tosilate, or a pharmaceutically acceptable derivative thereof, per day, such as 1 to 10 mg, such as 10 to 20 mg, 20 to 40 mg, 40 to 60 mg, 60 to 80 mg, 80 to 100 mg, 100 to 150 mg, 150 to 200 mg, 200 to 250 mg, 250 to 300 mg, 300 to 350 mg, 350 to 400 mg, 400 to 500 mg, 500 to 600 mg, 600 to 700 mg, 700 to 800 mg, 800 to 900 mg, 900 to 1000 mg, 1000 to 1250 mg, 1250 to 1500 mg, 1500 to 1750 mg, 1750 to 2000 mg, 2000 to 2250 md, 2250 to 2500 mg, 2500 to 2750 mg, 2750 to 3000 mg, 3000 to 3500 mg, 3500 to 4000 mg, for example 4000 to 5000 mg suplatast tosilate, or a pharmaceutically acceptable derivative thereof, per day.

Per day means the dosage may be given in one dosage or divided in multiple dosages per day, including once a day (QD), twice a day (BID), three times a day (TID) and/or four times a day (QID). In a preferred embodiment the dosage is given in one dosage once a day (QD) or one dosage twice a day (BID).

In one embodiment the compound is administered in one dosage or divided in multiple dosages once a day (QD). In one embodiment the compound is administered 100 mg suplatast tosilate, or a pharmaceutically acceptable derivative thereof, QD, such as 150 mg QD, such as 200 mg QD, such as 250 mg QD, such as 300 mg QD, such as 400 mg QD, such as 500 mg QD, such as 600 mg QD, such as 700 mg QD, such as 750 mg QD, such as 800 mg QD, such as 900 mg QD, such as 1000 mg suplatast tosilate, or a pharmaceutically acceptable derivative thereof, QD.

In one embodiment the compound is administered 100-1500 mg suplatast tosilate, or a pharmaceutically acceptable derivative thereof, QD; such as 100-200 mg QD, such as 200-300 mg QD, such as 300-400 mg QD, such as 400-500 mg QD, such as 500-600 mg QD, such as 600-700 mg QD, such as 700-800 mg QD, such as 800-900 mg QD, such as 900-1000 mg QD, such as 1000-1100 mg QD, such as 1100-1200 mg QD, such as 1200-1300 mg QD, such as 1300-1400 mg QD, such as 1400-1500 mg suplatast tosilate, or a pharmaceutically acceptable derivative thereof, QD.

In one embodiment the compound is administered in one dosage or divided in multiple dosages twice a day (BID). In one embodiment the compound is administered 100 mg suplatast tosilate, or a pharmaceutically acceptable derivative thereof, BID, such as 150 mg BID, such as 200 mg BID, such as 250 mg BID, such as 300 mg BID, such as 400 mg BID, such as 500 mg BID, such as 600 mg BID, such as 700 mg BID, such as 750 mg BID, such as 800 mg BID, such as 900 mg BID, such as 1000 mg suplatast tosilate, or a pharmaceutically acceptable derivative thereof, BID.

In one embodiment the compound is administered 100-1500 mg suplatast tosilate, or a pharmaceutically acceptable derivative thereof, BID; such as 100-200 mg BID, such as 200-300 mg BID, such as 300-400 mg BID, such as 400-500 mg BID, such as 500-600 mg BID, such as 600-700 mg BID, such as 700-800 mg BID, such as 800-900 mg BID, such as 900-1000 mg BID, such as 1000-1100 mg BID, such as 1100-1200 mg BID, such as 1200-1300 mg BID, such as 1300-1400 mg BID, such as 1400-1500 mg suplatast tosilate, or a pharmaceutically acceptable derivative thereof, BID.

In another embodiment the compound is administered in an amount of 0.01 mg/kg bodyweight suplatast tosilate, or a pharmaceutically acceptable derivative thereof, to 40 mg/kg bodyweight suplatast tosilate, or a pharmaceutically acceptable derivative thereof, such as 0.01 mg/kg bodyweight to 0.05 mg/kg bodyweight, 0.05 to 0.1 mg/kg bodyweight, 0.1 to 0.5 mg/kg bodyweight, 0.5 mg to 1 mg/kg bodyweight, 1 to 2 mg/kg bodyweight, 2 to 3 mg/kg bodyweight, 3 to 5 mg/kg bodyweight, 5 to 10 mg/kg bodyweight, 10 to 15 mg/kg bodyweight, 15 to 20 mg/kg bodyweight, 20 to 30 mg/kg bodyweight, for example 30 to 40 mg/kg bodyweight.

EXAMPLES

The present invention is further illustrated by the following examples which, however, are not to be construed as limiting the scope of protection.

Example 1

Sustained Release (SR) Suplatast Tosilate Mini-Tablets

Suplatast tosilate is mixed with Microcrystalline cellulose, L-HPC (Low-substituted HydroxyPropylCellulose) and a Croscarmellose for 5 min. in a tumble mixer. Next magnesium stearate is added and mixed in for 30 sec. The mix is compressed to tablets, each tablet with a tablet weight of 7.5 mg and size 2 mm each holding 3.00 mg suplatast tosilate. Tablet thickness is around 1.8 mm.

| Suplatast tosilate | 200.00 g |
| Microcrystalline cellulose | 120.00 g |
| L-HPC | 125.00 g |
| Croscarmellose | 50.00 g |
| Magnesium stearate | 5.00 g |
| Total | 500.00 |

Suplatast tosilate mini-tablets are film-coated in a fluid bed with a semi-permeable film based on Ethyl cellulose. Film composition is given in the below table. For 325 g core tablets, 1000 g of film solution is produced to be able to film coat to the desired increase in tablet weight of up to 25.0% incl. 5% overage for production loss. Spraying conditions are controlled to an outlet air temperature of 28-30° C. To reach the desired weight gain of 20%, 23% and 25%, 682.0 g, 784.9 g and 853.1 g film solution has to be applied respectively.

| Ethyl cellulose 7 cps | 100.0 |
| Ethanol 96% | 900.0 |
| Total | 1000.0 |

33 Mini-tablets, corresponding to 100 mg suplatast tosilate, are tested for dissolution using an USP2 Paddle apparatus (USP Paddle Dissolution Test Method). Each vessel contained 600 ml isotonic sodium chloride solution and stirred at 75 rpm. Expected release is given in FIG. 2.

Example 2

Sustained Release (SR) Suplatast Tosilate Mini-Tablets

Suplatast tosilate is mixed with Microcrystalline cellulose, Sodium starch glycolate and Pre-gelatinized starch for 2 min. in a 1 L high shear mixer. Purified water is added slowly over 2-3 min. while mixing until proper humidity is achieved and then granulated for 1 min. The produced granulate is dried in a STREA fluid-bed at approx. 60° C. until water activity is below 20% and sieved through a 1.4 mm screen.

| Suplatast tosilate | 72.74 g |
| Microcrystalline cellulose | 71.26 g |
| Sodium starch glycolate type A | 18.00 g |
| Pre-gelatinized starch | 18.00 g |
| Purified water | 121 g |
| Total | 180.0 g |

The produced suplatast tosilate granulate is mixed with Magnesium stearate. The mix is compressed to tablets, each tablet with a tablet weight of approx. 7.50 mg and size 2 mm each holding 3.0 mg suplatast tosilate. Tablet thickness was around 1.8 mm

| Suplatast tosilate granulate | 346.50 g |
| Magnesium stearate | 3.50 g |
| Total | 350.0 g |

Mini-tablets were film-coated in a fluid bed with a semi-permeable film based on Ethyl cellulose. Film composition is given in the below table. For 325 g core tablets, 600 g of film solution is produced to be able to film coat to the desired increase in tablet weight of up to 17.5% incl. 5% overage for production loss. Spraying conditions are controlled to an outlet air temperature of 28-30° C. To reach the desired weight gain of 12.5%, 15% and 17.5%, 426.6 g, 511.9 g and 597.2 g film solution has to be applied respectively.

| Ethyl cellulose 7 cps | 54.00 g |
| Hypromellose 3 | 6.00 g |
| Ethanol 96% | 405.00 g |
| Water | 135.00 g |
| Total | 600.0 g |

33 Mini-tablets, corresponding to 100 mg suplatast tosilate, are tested for dissolution using an USP2 Paddle apparatus (USP Paddle Dissolution Test Method). Each vessel contained 600 ml isotonic sodium chloride solution and stirred at 75 rpm. Expected release is given in FIG. 3.

Example 3

Immediate Release (IR) Suplatast Tosilate Mini-Tablets

Mini-tablets from Example 1 were film-coated in a fluid bed with a soluble film based on Hypromellose. Film composition is given in the below table. For 325 g core tablets, 200 g of film solution is produced to be able to film coat to the desired increase in tablet weight of up to 3% incl. 5% overage for production loss. Spraying conditions are controlled to an outlet air temperature of 40-42° C. To reach the desired weight gain of 3%, 186.0 g film solution is applied.

| | |
|---|---|
| Hypromellose 15 | 10.00 g |
| Polyethylene glycol 6000 | 1.00 g |
| Purified water | 189.00 g |
| Total | 200.0 g |

33 Mini-tablets, corresponding to 100 mg suplatast tosilate, are tested for dissolution using an USP2 Paddle apparatus (USP Paddle Dissolution Test Method). Each vessel contained 600 ml isotonic sodium chloride solution and stirred at 75 rpm. Expected release is given in FIG. 4.

Example 4

Immediate Release (IR) and Sustained Release (SR) Suplatast Tosilate Mini-Tablets in Capsules 33 immediate release (IR) suplatast tosilate mini-tablets from Example 3 and 33 film-coated sustained release (SR) suplatast tosilate mini-tablets from Example 2 are mixed and filled into a hard shell gelatine capsule size 00. The capsule then holds a dose of 100 mg suplatast tosilate IR+100 mg suplatast tosilate SR where the active components are released with a dose at start and the rest of the dose over 24 hours. Dosing regimen is two times a day.

Example 5

Immediate Release (IR) and Sustained Release (SR) Suplatast Tosilate Mini-Tablets in Capsules 33 immediate release (IR) suplatast tosilate mini-tablets from Example 3 and 167 film-coated sustained release (SR) suplatast tosilate mini-tablets from Example 1 are mixed and filled into three hard shell gelatine capsule size 00. The capsule then holds a dose of 100 mg suplatast tosilate IR+500 mg suplatast tosilate SR where the active components are released with a dose at start and the rest of the dose over 24 hours. Dosing regimen is once daily.

Example 6

Immediate Release (Coating) and Sustained Release (Core) Coated Tablets

Suplatast tosilate is mixed with Microcrystalline cellulose and Hypromellose 4000 for two min. in a 1 L high shear mixer. Purified water is added slowly over 10-12 min. while mixing until proper humidity is achieved and then granulated for 1 min. The produced granulate is dried in a STREA fluid-bed at approx. 60° C. until water activity is below 40% and sieved through a 1.4 mm screen.

| | |
|---|---|
| Suplatast tosilate | 192.00 g |
| Hypromellose 4000 | 8.00 g |
| Microcrystalline cellulose | 40.00 g |
| Purified water | 85 g |
| Total | 240.0 g |

The produced suplatast tosilate granulate is mixed with Hypromellose 4000, Silicon dioxide and magnesium stearate. The mix is compressed to tablets, each tablet with a tablet weight of approx. 175.5 mg and size 8 mm each holding 100 mg suplatast tosilate.

| | |
|---|---|
| Suplatast tosilate granulate | 213.65 g |
| Hypromellose 4000 | 82.85 g |
| Silicon dioxide | 1.50 g |
| Magnesium stearate | 2.00 g |
| Total | 300.0 |

Suplatast tosilate tablets are film-coated in a perforated drum coater with a semi-permeable barrier film based on Ethyl cellulose. Film composition is given in the below table. For 225 g core tablets, 250 g of film solution is produced to be able to film coat to the desired increase in tablet weight of 7.0% incl. 10% overage for production loss. Spraying conditions are controlled to a product air temperature of 27-29° C. To reach the desired weight gain 173.25 g film solution is applied.

| | |
|---|---|
| Ethyl cellulose 7 cps | 20.00 g |
| Ethanol 96% | 168.75 g |
| Hypromellose 3 cps | 5.00 g |
| Purified water | 56.25 g |
| Total | 250.0 |

Barrier coated suplatast tosilate tablets are film-coated in a perforated drum coater with an immediate release film containing suplatast tosilate. Film composition is given in the below table. For 225 g core tablets, 800 g of film solution is produced to be able to film coat to the desired increase in tablet weight of 47.1% corresponding to 50 mg of suplatast tosilate. Spraying conditions are controlled to match a product air temperature of 40-42° C. To reach the desired weight gain 705.1 g film solution is applied incl. 10% overage for production loss.

| | |
|---|---|
| Suplatast tosilate | 80.00 g |
| Polyethylene glycol | 5.60 g |
| Hypromellose 15 cps | 56.00 g |
| Purified water | 658.40 g |
| Total | 800.0 g |

The tablets are tested for dissolution using an USP2 Paddle apparatus (USP Paddle Dissolution Test Method). Each vessel contained 600 ml isotonic sodium chloride solution and stirred at 75 rpm. The tablets then hold a dose of 50 mg suplatast tosilate IR+100 mg suplatast tosilate SR where the active components are released with a dose at start and the rest of the dose over 12 hours. Dosing regimen is two tablets two times a day.

Example 7

Immediate Release (Coating) and Sustained Release (Core) Coated Tablets

The suplatast tosilate granulate from Example 6 is mixed with Hypromellose 4000, Silicon dioxide and magnesium stearate as given in table below. The tablet mix is compressed to tablets, each tablet with a tablet weight of approx. 512.6 mg and size 12 mm each holding 250 mg suplatast tosilate.

| | |
|---|---|
| Suplatast tosilate granulate | 182.90 g |
| Hypromellose 4000 | 113.90 g |
| Silicon dioxide | 1.50 g |
| Magnesium stearate | 1.70 g |
| Total | 300.0 |

Suplatast tosilate tablets are film-coated in a perforated drum coater with a semi-permeable barrier film based on Ethyl cellulose. Film composition is given in the below table. For 225 g core tablets, 250 g of film solution is produced to be able to film coat to the desired increase in tablet weight of 6.0% incl. 10% overage for production loss. Spraying conditions are controlled to a product air temperature of 27-29° C. To reach the desired weight gain 185.625 g film solution is applied.

| | |
|---|---|
| Ethyl cellulose 7 cps | 22.50 g |
| Ethanol 96% | 215.625 g |
| Hypromellose 3 cps | 2.50 g |
| Purified water | 71.875 g |
| Total | 250.0 |

Barrier coated suplatast tosilate tablets are film-coated in a perforated drum coater with an immediate release film containing suplatast tosilate. Film composition is given in the below table. For 225 g core tablets, 525 g of film solution is produced to be able to film coat to the desired increase in tablet weight of 21.9% corresponding to 50 mg of suplatast tosilate. Spraying conditions are controlled to match a product air temperature of 40-42° C. To reach the desired weight gain 422.5 g film solution is applied incl. 10% overage for production loss.

| | |
|---|---|
| Suplatast tosilate | 30.00 g |
| Polyethylene glycol | 3.75 g |
| Hypromellose 15 cps | 37.50 g |
| Purified water | 453.75 g |
| Total | 525.0 g |

The tablets are tested for dissolution using an USP2 Paddle apparatus (USP Paddle Dissolution Test Method). Each vessel contained 600 ml isotonic sodium chloride solution and stirred at 75 rpm. The tablets then hold a dose of 50 mg suplatast tosilate IR+250 mg suplatast tosilate SR where the active components are released with a dose at start and the rest of the dose over 24 hours. Dosing regimen is two tablets once a day.

Example 8

Immediate Release and Sustained Release Bi-Layer Tablets

The suplatast tosilate granulate from Example 6 is mixed with Microcrystalline cellulose, Lactose, Croscarmellose and Magnesium stearate as given in table below to constitute tablet mix IR.

| | |
|---|---|
| Suplatast tosilate granulate | 125.00 g |
| Microcrystalline cellulose | 35.00 g |
| Lactose | 36.00 g |
| Croscarmellose | 3.00 g |
| Magnesium stearate | 1.00 g |
| Total | 200.0 |

Suplatast tosilate granulate from Example 6 is mixed with Hypromellose 4000, Sodium Carboxymethylcellulose and magnesium stearate as given in table below to constitute tablet mix SR.

| | |
|---|---|
| Suplatast tosilate granulate | 250.00 g |
| Hypromellose 4000 | 190.00 g |
| Sodium Carboxymethylcellulose | 58.00 g |
| Magnesium stearate | 2.00 g |
| Total | 500.0 |

The tablet mix SR is compressed as layer 1 (500 mg) and the tablet mix IR is compressed as layer 2 (200 mg) on a bi-layer tablet press. Each tablet weight approx. 700 mg, each holding 100 mg suplatast tosilate for immediate release and 200 mg suplatast tosilate for release over 12 hours.

The tablets are tested for dissolution using an USP2 Paddle apparatus (USP Paddle Dissolution Test Method). Each vessel contained 600 ml isotonic sodium chloride solution and stirred at 75 rpm. The tablets then hold a dose of 100 mg suplatast tosilate IR+200 mg suplatast tosilate SR where the active components are released with a dose at start and the rest of the dose over 12 hours. Dosing regimen is one tablet twice a day.

Example 9

Immediate Release and Sustained Release Press-Coated Tablets

Suplatast tosilate granulate from Example 6 is mixed with Hypromellose 4000, Sodium Carboxymethylcellulose and magnesium stearate as given in table below to constitute tablet mix SR. The tablet mix SR is compressed to SR tablets, each tablet with a tablet weight of approx. 196 mg and size 8 mm each holding 100 mg suplatast tosilate.

| | |
|---|---|
| Suplatast tosilate granulate | 213.65 g |
| Hypromellose 4000 | 82.85 g |
| Sodium Carboxymethylcellulose | 36.50 g |
| Magnesium stearate | 2.00 g |
| Total | 335.0 |

Suplatast tosilate granulate from Example 6 is mixed with Microcrystalline cellulose, Lactose, Croscarmellose and Magnesium stearate as given in table below to constitute tablet mix IR. The tablet mix IR is used as outer layer and the SR tablets are applied as tablet cores using a special tablet press for compression coating, which is also known as press coating or tablet in tablet. Outer IR layer must have a weight of approx. 400 mg and holding 100 mg suplatast tosilate. Total weight of compression coated tablet will therefore be approx. 596 mg.

| Suplatast tosilate granulate | 125.00 g |
|---|---|
| Microcrystalline cellulose | 80.00 g |
| Lactose | 185.00 g |
| Croscarmellose | 8.00 g |
| Magnesium stearate | 2.00 g |
| Total | 335.0 |

The tablets are tested for dissolution using an USP2 Paddle apparatus (USP Paddle Dissolution Test Method). Each vessel contained 600 ml isotonic sodium chloride solution and stirred at 75 rpm. The tablet then holds a dose of 100 mg suplatast tosilate IR+100 mg suplatast tosilate SR where the active components are released with a dose at start and the rest of the dose over 12 hours. Dosing regimen is one tablet twice a day.

Example 10

Suplatast tosilate was mixed with Microcrystalline cellulose, Sodium starch glycolate and pre-gelatinized starch for 2 min. in a 1 L high shear mixer. A 0.1% solution of citric acid in purified water was added slowly over 2-3 min. while mixing until proper humidity was achieved and then granulated for 1 min. The produced granulate was wet screened through a 1.7 mm screen and dried in a cabinet at approx. 40° C. for about 90 minutes. The granulate was then sieved though a 0.7 mm screen. Water activity was approx. 23%.

| Suplatest tosilate | 20.21 g |
|---|---|
| Microcrystalline cellulose | 19.80 g |
| Sodium starch glycolate type A | 5.00 g |
| Pre-gelatinized starch | 5.00 g |
| Citric acid monohydrate | 0.012 g |
| Purified water | 12.0 g |
| Total | 50.0 g |

The produced suplatast tosilate granulate was mixed with Magnesium stearate. The mix was compressed to tablets, each tablet with a tablet weight of approx. 7.60 mg and size 2 mm each holding 2.0 mg Suplatast base. Tablet thickness was around 2.0 mm

| Suplatast tosilate granulate | 346.50 g |
|---|---|
| Magnesium stearate | 3.50 g |
| Total | 350.0 g |

Mini-tablets were film coated in a fluid bed with a semi-permeable film based on Ethyl cellulose. Film composition is given in the below table. For 325 g core tablets, 600 g of film solution was produced to be able to film coat to the desired increase in tablet weight of 15% incl. 5% overage for production loss. Spraying conditions were controlled to an outlet air temperature of 28-30° C. To reach the desired weight gain of 15%, 511.9 g film solution was applied respectively.

| Ethyl cellulose 7 cps | 54.00 g |
|---|---|
| Hypromellose 3 | 6.00 g |
| Ethanol 96% | 405.00 g |
| Water | 135.00 g |
| Total | 600.0 g |

50 Mini-tablets, corresponding to 100 mg suplatast base, were tested for dissolution using an USP2 Paddle apparatus (USP Paddle Dissolution Test Method). Each vessel contained 600 ml isotonic sodium chloride solution and stirred at 75 rpm. Samples were analyzed by UV at 280 nm. Release profile is given in FIG. 5.

Example 11

Suplatast tosilate was mixed with Microcrystalline cellulose, L-HPC and a Croscarmellose for 5 min. in a tumble mixer. Next magnesium stearate was added and mixed in for 30 sec. The mix was compressed to tablets, each tablet with a tablet weight of 6.7 mg and size 2 mm each holding 1.75 mg suplatast base. Tablet thickness was around 1.9 mm.

| Suplatest tosilate | 200.00 g |
|---|---|
| Microcrystalline cellulose | 120.00 g |
| L-HPC | 125.00 g |
| Croscarmellose | 50.00 g |
| Magnesium stearate | 5.00 g |
| Total | 500.00 |

Mini-tablets were film coated in a fluid bed with a soluble film based on Hypromellose. Film composition is given in the below table. For 325 g core tablets, 200 g of film solution was produced to be able to film coat to the desired increase in tablet weight of up to 3% incl. 5% overage for production loss. Spraying conditions were controlled to an outlet air temperature of 34-36° C. To reach the desired weight gain of 3%, 186.0 g film solution was applied.

| Hypromellose 15 | 10.00 g |
|---|---|
| Polyethylene glycol 6000 | 1.00 g |
| Purified water | 189.00 g |
| Total | 200.0 g |

57 Mini-tablets, corresponding to 100 mg Suplatast base, were tested for dissolution using an USP2 Paddle apparatus (USP Paddle Dissolution Test Method). Each vessel contained 600 ml isotonic sodium chloride solution and stirred at 75 rpm. Samples were analyzed by UV at 280 nm. Release profile is given in FIG. 6.

Example 12

57 immediate release (IR) suplatast tosilate mini-tablets from Example 11 and 50 film coated sustained release (SR) suplatast tosilate mini-tablets from Example 10 were mixed and filled into a hard shell gelatine capsule size 000. The capsule then holds a dose of 100 mg suplatast base IR+100 mg suplatast base SR where the active components were released with a dose at start and the rest of the dose over 12 hours. Dosing regimen is two times a day. Capsules were tested for dissolution using an USP2 Paddle apparatus (USP Paddle Dissolution Test Method). Each vessel contained 600 ml isotonic sodium chloride solution and stirred at 75 rpm. Samples were analyzed by UV at 280 nm. Release profile is given in FIG. 7.

Example 13

Suplatast tosilate was mixed with Microcrystalline cellulose and Hypromellose 4000 for two min. in a 1 L high shear mixer. A 0.1% solution of citric acid in Purified water was added slowly over 13 min. while mixing until proper humidity was. The produced granulate was dried in a cabinet at 40° C. for 12 hours. The granulate was sieved through a 1.0 mm screen.

| | |
|---|---|
| Suplatest tosilate | 128.00 g |
| Hypromellose 4000 | 5.33 g |
| Microcrystalline cellulose | 26.67 g |
| Citric acid monohydrate | 0.025 g |
| Purified water | 25 g |
| Total | 160.0 g |

The produced Suplatast granulate was mixed with Hypromellose 4000, Silicon dioxide and magnesium stearate. The mix was compressed to tablets om 8 mm round tooling, each tablet with a tablet weight of approx. 267 mg each holding 100 mg Suplatast base.

| | |
|---|---|
| Suplatast granulate | 213.65 g |
| Hypromellose 4000 | 82.85 g |
| Silicon dioxide | 1.50 g |
| Magnesium stearate | 2.00 g |
| Total | 300.0 |

Suplatast tablets were film coated in a perforated drum coater with a semi-permeable barrier film based on Ethyl cellulose. Film composition is given in the below table. For 200 g core tablets, 250 g of film solution was produced to be able to film coat to the desired increase in tablet weight of 7.0% incl. 10% overage for production loss. Spraying conditions were controlled to a product air temperature of 27-29° C. To reach the desired weight gain 154 g film solution was applied.

| | |
|---|---|
| Ethyl cellulose 7 cps | 20.00 g |
| Ethanol 96% | 168.75 g |
| Hypromellose 3 cps | 5.00 g |
| Purified water | 56.25 g |
| Total | 250.0 |

Barrier coated Suplatast tablets were film coated in a perforated drum coater with an immediate release film containing suplatast tosilate. Film composition is given in the below table. For 200 g core tablets, 600 g of film solution was produced to be able to film coat to the desired 50 mg of Suplatast base. Spraying conditions were controlled to match a product air temperature of 40-42° C. To reach the desired dose of suplatast base, 598.1 g film solution is applied incl. 5% overage for production loss.

| | |
|---|---|
| Suplatest tosilate | 60.00 g |
| Polyethylene glycol | 4.20 g |
| Hypromellose 15 cps | 43.00 g |
| Purified water | 511.80 g |
| Total | 600.0 g |

The tablets were tested for dissolution using an USP2 Paddle apparatus (USP Paddle Dissolution Test Method). Each vessel contained 600 ml isotonic sodium chloride solution and stirred at 75 rpm. Samples were analyzed by UV at 280 nm. The tablets then contained 50 mg suplatast base IR+100 mg suplatast base SR where the active components are released with a dose at start and the rest of the dose over 12 hours. Dosing regimen is two tablets two times a day. Release profile is given in FIG. 8.

Example 14

The Suplatast granulate from Example 13 was mixed with Hypromellose 4000, Silicon dioxide and magnesium stearate as given in table below. The tablet mix was compressed to tablets om 8×18.8 mm oval tooling, each tablet with a tablet weight of approx. 779.5 mg each holding 250 mg Suplatast base.

| | |
|---|---|
| Suplatast granulate | 182.90 g |
| Hypromellose 4000 | 113.90 g |
| Silicon dioxide | 1.50 g |
| Magnesium stearate | 1.70 g |
| Total | 300.0 |

Suplatast tablets were film coated in a perforated drum coater with a semi-permeable barrier film based on Ethyl cellulose. Film composition is given in the below table. For 225 g core tablets, 250 g of film solution was produced to be able to film coat to the desired increase in tablet weight of 6.0% incl. 10% overage for production loss. Spraying conditions were controlled to a product air temperature of 27-29° C. To reach the desired weight gain 165.0 g film solution was applied.

| | |
|---|---|
| Ethyl cellulose 7 cps | 18.00 g |
| Ethanol 96% | 172.50 g |
| Hypromellose 3 cps | 2.00 g |
| Purified water | 57.50 g |
| Total | 250.0 |

Barrier coated Suplatast tablets were film coated in a perforated drum coater with an immediate release film containing suplatast tosilate. Film composition is given in the below table. For 225 g core tablets, 400 g of film solution was produced to be able to film coat to the desired increase in tablet weight corresponding to 50 mg of suplatast base. Spraying conditions were controlled to match a product air temperature of 40-42° C. To reach the desired weight gain 358.5 g film solution was applied incl. 5% overage for production loss.

| | |
|---|---|
| Suplatest tosilate | 22.86 g |
| Polyethylene glycol | 2.86 g |
| Hypromellose 15 cps | 28.57 g |
| Purified water | 345.70 g |
| Total | 400.0 g |

The tablets were tested for dissolution using an USP2 Paddle apparatus (USP Paddle Dissolution Test Method). Each vessel contained 600 ml isotonic sodium chloride solution and stirred at 75 rpm. Samples were analyzed by UV at 280 nm. The tablets then holds a dose of 50 mg suplatast base IR+250 mg suplatast base SR where the active components were released with a dose at start and the rest of the dose over time. Release profile is given in FIG. 9.

Release time may be adjusted to faster release by adjusting film thickness of barrier coating.

Example 15

The Suplatast granulate from Example 13 was mixed with Microcrystalline cellulose, Lactose, Croscarmellose and Magnesium stearate as given in table below to constitute tablet mix IR.

| | |
|---|---|
| Suplatast granulate | 125.00 g |
| Microcrystalline cellulose | 35.00 g |
| Lactose | 36.00 g |
| Croscarmellose | 3.00 g |
| Magnesium stearate | 1.00 g |
| Total | 200.0 |

Suplatast granulate from Example 13 is mixed with Hypromellose 4000, Sodium Carboxymethylcellulose and magnesium stearate as given in table below to constitute tablet mix SR.

| | |
|---|---|
| Suplatest granulate | 250.00 g |
| Hypromellose 4000 | 190.00 g |
| Sodium Carboxymethylcellulose | 58.00 g |
| Magnesium stearate | 2.00 g |
| Total | 500.0 |

The tablet mix SR is compressed as layer 1 (760 mg) and the tablet mix IR was compressed as layer 2 (304 mg) on a bi-layer tablet press using 10×22 mm tooling. Each tablet weight approx. 1064 mg, each holding 100 mg suplatast base for immediate release and 200 mg suplatast base for release over 12 hours.

The tablets were tested for dissolution using an USP2 Paddle apparatus (USP Paddle Dissolution Test Method). Each vessel contained 600 ml isotonic sodium chloride solution and stirred at 75 rpm. Samples were analyzed by UV at 280 nm. The tablet then holds a dose of 100 mg suplatast base IR+200 mg suplatast base SR where the active components were released with a dose at start and the rest of the dose over 12 hours. Release profile is given in FIG. 10. Dosing regimen is one tablet twice a day.

The invention claimed is:

1. A pharmaceutical composition comprising
   a. a first release component which comprises a plurality of extended-release film-coated mini-tablets comprising a semi-permeable film or extended-release film-coated pellets comprising a semi-permeable film, and comprising a compound selected from suplatast tosilate, or a pharmaceutically acceptable salt, ester, prodrug, precursor or crystal thereof, and providing for extended release of said compound, and
   b. a second release component which comprises a plurality of immediate-release film-coated mini-tablets comprising a soluble film or immediate-release film-coated pellets comprising a soluble film, and comprising a compound selected from suplatast tosilate, or a pharmaceutically acceptable salt, ester, prodrug, precursor or crystal thereof, and providing for immediate release of said compound,
wherein said composition comprises the first release component and the second release component in separate compartments.

2. The composition according to claim 1, wherein said suplatast tosilate is selected from the group consisting of a racemic compound, a (+)-suplatast tosilate enantiomer and a (−)-suplatast tosilate enantiomer.

3. The composition according to claim 1, wherein said pharmaceutical composition is a pharmaceutical dosage form is an oral solid dosage form.

4. The composition according to claim 1, wherein said composition is a multiparticulate dosage form comprising, separately or together, two or more dosage forms.

5. The composition according to claim 1, wherein said composition comprises
   a. the first release component which is a plurality of extended-release film-coated mini-tablets comprising a semi-permeable film, and
   b. the second release component which is a plurality of immediate-release film-coated mini-tablets comprising a soluble film.

6. The composition according to claim 1, wherein
   said first and second release components are provided together in an appropriate container such as a capsule, a pouch a sachet or a stick pack.

7. The composition according to claim 1, wherein immediate release from the second release component occurs first, followed by and optionally overlapping with, extended release from the first release component.

8. The composition according to claim 1, wherein immediate release from the second release component and extended release from the first release component occurs simultaneously.

9. The composition according to claim 1, wherein extended release from the first release component occurs first, followed by and optionally overlapping with, immediate release from the second release component.

10. The composition according to claim 1, wherein the first release component (ER) comprises a dosage of 50-500 mg suplatast tosilate, or a pharmaceutically acceptable salt, ester, prodrug, precursor or crystal thereof, such as 50-100 mg, 100-150 mg, 150-200 mg, 200-250 mg, 250-300 mg, 300-350 mg, 350-400 mg, 400-450 mg, 450-500 mg; such as 50 mg, 100 mg, 150 mg, 200 mg, 250 mg, 300 mg, 350 mg, 400 mg, 450 mg or 500 mg suplatast tosilate, or a pharmaceutically acceptable salt, ester, prodrug, precursor or crystal thereof; and
   the second release component (IR) comprises a dosage of 25-250 mg suplatast tosilate, or a pharmaceutically acceptable salt, ester, prodrug, precursor or crystal thereof, such as 25-50 mg, 50-75 mg, 75-100 m, 100-150 mg, 150-200 mg, 200-250 mg; such as 25 mg, 50 mg, 75 mg, 100 mg, 150 mg, 200 mg or 250 mg suplatast tosilate, or a pharmaceutically acceptable salt, ester, prodrug, precursor or crystal thereof.

11. The composition according to claim 1, wherein said first release component comprises one or more release-controlling excipients providing for extended release.

12. The composition according to claim 1, wherein said second release component comprises an excipient providing for immediate release, such as a film-forming excipient.

13. The composition according to claim 1, wherein said composition comprises, separately or together, one or more further active pharmaceutical ingredients.

14. The composition according to claim 1, wherein said semi-permeable film comprises ethylcellulose and wherein said soluble film comprises hypromellose.

15. The composition according to claim 14, wherein said semi-permeable film comprises ethylcellulose and ethanol, or comprises ethylcellulose, hypromellose and ethanol; and wherein said soluble film comprises hypromellose and polyethylene glycol.

16. The composition according to claim 1, wherein said first release component is film-coated with a semi-permeable film added to a weight gain of 15 to 25%.

17. The composition according to claim 1, wherein composition according to any of the preceding claims, wherein said second release component is film-coated with a soluble film added to a weight gain of up to 3%.

18. The composition according to claim 1, wherein the first release component is a film-coated mini-tablet or pellet comprising one or more of: suplatast tosilate, microcrystalline cellulose, L-HPC, a croscarmellose, and magnesium stearate,
  wherein the film-coating comprises a semi-permeable film comprising ethylcellulose.

19. The composition according to claim 1, wherein the first release component is a film-coated mini-tablet or pellet comprising one or more of suplatast tosilate, microcrystalline cellulose, Sodium starch glycolate (type A), pre-gelatinized starch, citric acid monohydrate, and magnesium stearate,
  wherein the film-coating comprises a semi-permeable film comprising ethylcellulose.

20. The composition according to claim 1, wherein the second release component is a film-coated mini-tablet or pellet comprising one or more of suplatast tosilate, microcrystalline cellulose, L-HPC, a croscarmellose, and magnesium stearate, wherein the film-coating comprises a soluble film comprising hypromellose.

* * * * *